(12) United States Patent
Bar-Or et al.

(10) Patent No.: US 9,410,913 B2
(45) Date of Patent: Aug. 9, 2016

(54) METHODS AND SYSTEMS FOR MEASURING AND USING THE OXIDATION-REDUCTION POTENTIAL OF A BIOLOGICAL SAMPLE

(71) Applicant: Aytu BioScience, Inc., Englewood, CO (US)

(72) Inventors: Raphael Bar-Or, Denver, CO (US); David Bar-Or, Englewood, CO (US); Leonard T. Rael, Centennial, CO (US)

(73) Assignee: AYTU BIOSCIENCE, INC., Englewood, CO (US)

( * ) Notice: Subject to any disclaimer, the term of this patent is extended or adjusted under 35 U.S.C. 154(b) by 162 days.

(21) Appl. No.: 14/061,436

(22) Filed: Oct. 23, 2013

(65) Prior Publication Data

US 2014/0110273 A1     Apr. 24, 2014

Related U.S. Application Data

(60) Provisional application No. 61/717,511, filed on Oct. 23, 2012, provisional application No. 61/868,983, filed on Aug. 22, 2013.

(51) Int. Cl.
*G01N 27/327* (2006.01)
*G01N 27/26* (2006.01)
(Continued)

(52) U.S. Cl.
CPC ............ *G01N 27/26* (2013.01); *G01N 27/4168* (2013.01); *G01N 33/48* (2013.01)

(58) Field of Classification Search
CPC ..... G01N 27/48; G01N 27/26; G01N 27/327; G01N 33/487; A61B 5/05; A61B 5/14532; C12Q 1/00; C12Q 1/02; C12Q 1/34; C12Q 1/54; G01R 17/02; H01J 49/0036
See application file for complete search history.

(56) References Cited

U.S. PATENT DOCUMENTS 3,956,094 A    5/1976  Capuano
4,053,381 A   10/1977  Hamblen et al.
(Continued)

FOREIGN PATENT DOCUMENTS

CN    1301343    6/2001
CN    1776414    5/2006
(Continued)

OTHER PUBLICATIONS

International Search Report and Written Opinion for International Patent Application No. PCT/US13/66432, mailed May 13, 2014, 16 pages.
(Continued)

*Primary Examiner* — Jennifer Dieterle
(74) *Attorney, Agent, or Firm* — Sheridan Ross P.C.

(57) ABSTRACT

Methods and systems for measuring and using the oxidation-reduction characteristics of a biological sample are provided. The system generally includes a test strip and a readout device. A fluid sample is placed in the test strip, and the test strip is in turn operatively connected to the readout device. The readout device provides a controlled current that is sent across the fluid in the sample chamber. In addition, the read-out device identifies an inflection point or transition time at which the voltage between contacts of the test strip is changing at the highest rate. The oxidation-reduction capacity of the sample is taken as the integral of the current profile from the time at which current begins to be supplied to the sample to the identified transition time.

4 Claims, 6 Drawing Sheets

(51) Int. Cl.
*G01N 27/416* (2006.01)
*G01N 33/48* (2006.01)

(56) References Cited

U.S. PATENT DOCUMENTS

| | | | |
|---|---|---|---|
| 4,225,410 A | 9/1980 | Pace | |
| 4,299,919 A | 11/1981 | Jellinek | |
| 4,545,382 A | 10/1985 | Higgins et al. | |
| 4,571,292 A | 2/1986 | Liu et al. | |
| 4,865,717 A | 9/1989 | Setter et al. | |
| 4,963,245 A | 10/1990 | Weetall | |
| 4,980,043 A | 12/1990 | Tomita et al. | |
| 5,073,011 A | 12/1991 | Ito et al. | |
| 5,165,406 A | 11/1992 | Wong | |
| 5,228,972 A | 7/1993 | Osaka et al. | |
| 5,230,786 A | 7/1993 | Preidel | |
| 5,260,321 A | 11/1993 | Hof et al. | |
| 5,267,569 A | 12/1993 | Lienhard | |
| 5,273,639 A | 12/1993 | Kaneko et al. | |
| 5,290,519 A | 3/1994 | Bar-Or et al. | |
| 5,312,590 A | 5/1994 | Gunasingham | |
| 5,334,305 A | 8/1994 | Okada et al. | |
| 5,384,031 A | 1/1995 | Anderson et al. | |
| 5,393,391 A | 2/1995 | Dietze et al. | |
| 5,395,755 A | 3/1995 | Thorpe et al. | |
| 5,401,376 A | 3/1995 | Foos et al. | |
| 5,509,410 A | 4/1996 | Hill et al. | |
| 5,562,815 A | 10/1996 | Preidel | |
| 5,582,698 A | 12/1996 | Flaherty et al. | |
| 5,645,709 A | 7/1997 | Birch et al. | |
| 5,656,142 A | 8/1997 | Park et al. | |
| 5,672,811 A | 9/1997 | Kato et al. | |
| 5,679,532 A | 10/1997 | Repine | |
| 5,728,281 A | 3/1998 | Holmstrom et al. | |
| 5,782,879 A | 7/1998 | Rosborough et al. | |
| 5,799,350 A | 9/1998 | Ferek-Petric et al. | |
| 5,820,551 A | 10/1998 | Hill et al. | |
| 5,906,921 A | 5/1999 | Ikeda et al. | |
| 6,143,164 A | 11/2000 | Heller et al. | |
| 6,177,260 B1 | 1/2001 | Benzie et al. | |
| 6,212,417 B1 | 4/2001 | Ikeda et al. | |
| 6,236,873 B1 | 5/2001 | Holmstrom | |
| 6,269,261 B1 | 7/2001 | Ootomo | |
| 6,280,588 B1 | 8/2001 | Kato et al. | |
| 6,294,062 B1 | 9/2001 | Buck, Jr. et al. | |
| 6,321,101 B1 | 11/2001 | Holmstrom | |
| 6,340,428 B1 | 1/2002 | Ikeda et al. | |
| 6,369,106 B1 | 4/2002 | Atlas et al. | |
| 6,429,021 B1 | 8/2002 | Qian et al. | |
| 6,447,670 B1 | 9/2002 | Holmstrom | |
| 6,599,746 B1 | 7/2003 | Gumbrecht | |
| 6,607,658 B1 | 8/2003 | Heller et al. | |
| 6,720,107 B1 | 4/2004 | Holtom et al. | |
| 6,749,740 B2 | 6/2004 | Liamos et al. | |
| 6,790,327 B2 | 9/2004 | Ikeda et al. | |
| 6,793,632 B2 | 9/2004 | Sohrab | |
| 7,063,782 B2 | 6/2006 | Wayment et al. | |
| 7,125,723 B2 | 10/2006 | Popov et al. | |
| 7,132,296 B2 | 11/2006 | Ou et al. | |
| 7,134,602 B2 | 11/2006 | Harima | |
| 7,267,750 B2 | 9/2007 | Watanabe et al. | |
| 7,459,066 B2 | 12/2008 | Broadley et al. | |
| 7,618,522 B2 | 11/2009 | Davies | |
| 7,949,473 B2 | 5/2011 | Rauh | |
| 8,317,997 B2 | 11/2012 | Bar-Or et al. | |
| 8,329,012 B2 | 12/2012 | Bar-Or et al. | |
| 8,512,548 B2 | 8/2013 | Bar-Or et al. | |
| 8,641,888 B2 | 2/2014 | Bar-Or et al. | |
| 9,034,159 B2 | 5/2015 | Bar-Or et al. | |
| 2002/0053523 A1* | 5/2002 | Liamos | G01N 27/3272 205/787 |
| 2002/0115619 A1 | 8/2002 | Rubenstein et al. | |
| 2004/0171112 A1 | 9/2004 | Remington et al. | |
| 2005/0074893 A1 | 4/2005 | Horiguchi et al. | |
| 2005/0142613 A1 | 6/2005 | Bar-Or et al. | |
| 2005/0182568 A1 | 8/2005 | Duraffourd et al. | |
| 2005/0244983 A1 | 11/2005 | Ching | |
| 2006/0006122 A1 | 1/2006 | Burns et al. | |
| 2006/0258973 A1 | 11/2006 | Volt | |
| 2007/0020181 A1 | 1/2007 | Workman et al. | |
| 2007/0111104 A1 | 5/2007 | Shibuya | |
| 2008/0052130 A1 | 2/2008 | Iliff | |
| 2008/0269167 A1 | 10/2008 | Ziegler et al. | |
| 2009/0000947 A1 | 1/2009 | Akahori et al. | |
| 2009/0004686 A1 | 1/2009 | Bar-Or et al. | |
| 2010/0267074 A1 | 10/2010 | Bar-Or et al. | |
| 2010/0270149 A1* | 10/2010 | Wang | A61M 5/1723 204/403.01 |
| 2012/0217159 A1* | 8/2012 | Bar-Or et al. | 204/403.02 |
| 2013/0277232 A1 | 10/2013 | Bar-Or et al. | |
| 2014/0121158 A1 | 5/2014 | Bar-Or et al. | |
| 2014/0291169 A1 | 10/2014 | Bar-Or et al. | |
| 2015/0219588 A1 | 8/2015 | Bar-Or et al. | |

FOREIGN PATENT DOCUMENTS

| | | |
|---|---|---|
| CN | 1875265 | 12/2006 |
| DE | 202005009988 | 10/2005 |
| EP | 0634488 | 1/1995 |
| JP | S60-62978 | 4/1985 |
| JP | H08-94574 | 4/1996 |
| JP | H08-509617 | 10/1996 |
| JP | H09-178690 | 7/1997 |
| JP | H09-304330 | 11/1997 |
| JP | H09-327443 | 12/1997 |
| JP | H10-232219 | 9/1998 |
| JP | H11-83797 | 3/1999 |
| JP | 2000-002683 | 1/2000 |
| JP | 2000-088801 | 3/2000 |
| JP | 2001-021527 | 1/2001 |
| JP | 2001-289812 | 10/2001 |
| JP | 2002-207037 | 7/2002 |
| JP | 2002-535615 | 10/2002 |
| JP | 2003-503702 | 1/2003 |
| JP | 2003-202317 | 7/2003 |
| JP | 2004-117084 | 4/2004 |
| JP | 2004-350861 | 12/2004 |
| JP | 2006-508349 | 3/2006 |
| JP | 2007-057459 | 3/2007 |
| JP | 3971997 | 9/2007 |
| JP | 2009-075127 | 4/2009 |
| JP | 2010-96724 | 4/2010 |
| JP | 2012-047647 | 3/2012 |
| RU | 2241997 | 12/2004 |
| WO | WO 94/25626 | 11/1994 |
| WO | WO 01/25776 | 4/2001 |
| WO | WO 03/071266 | 8/2003 |
| WO | WO 2004/068140 | 8/2004 |
| WO | WO 2007/039775 | 4/2007 |
| WO | WO 2007/059455 | 5/2007 |

OTHER PUBLICATIONS

International Preliminary Report on Patentability for International Patent Application No. PCT/US13/66432, mailed May 7, 2015, 12 pages.
International Preliminary Report on Patentability for International Patent Application No. PCT/US13/37357, mailed Oct. 30, 2014, 9 pages.
Abiles et al., "Oxidative stress is increased in critically ill patients according to antioxidant vitamins intake, independent of severity: a cohort study," Oct. 13, 2006, available online at www.ccforum.com/content/10/5/R146, 9 pages.
Alonso De Vega et al., "Oxidative Stress in Critically Ill Patients with Systemic Inflammatory Response Syndrome," Critical Care Medicine, vol. 30, No. 8 (Aug. 2002), pp. 1782-1786, (Abstract) 1 page.
Alonso De Vega et al., "Plasma Redox Status Relates to Severity in Critically Ill Patients," Critical Care Medicine, vol. 28, No. 6 (Jun. 2000), pp. 1812-1814, (Abstract) 1 page.
Ascensao et al., "Biochemical Impact of a Soccer Match—Analysis of Oxidative Stress and Muscle Damage Markers Throughout Recovery," Clinical Biochemistry, vol. 41, No. 10-11 (Jul. 2008), pp. 841-851, (Abstract) 1 page.

(56) References Cited

OTHER PUBLICATIONS

Author Unknown, "Glucose meter," available at www.en.wikipedia.org/wiki/Glucose_meter, printed on Jun. 14, 2009, 7 pages.
Author Unknown, "Materials for Diagnostic Assays," PALL Life Sciences, Mar. 2009, 8 pages.
Author Unknown, "Orion pH, ORP and ISE Theory," Thermo Electron Corporation, Mar. 24, 2004, 9 pages.
Author Unknown, "Oxidation Reduction Potential (ORP): A New Tool for Evaluating Water Sanitation", Hybrid, Hendrix Genetics Company, Dec. 17, 2010, 4 pages.
Author Unknown, "Redox electrode," Unisense Science, as late as Jun. 6, 2009, 2 pages.
Author Unknown, "Universal Reduction-Oxidation (REDOX) electrode for the Temporal Measurement of the Redox Potential Health and Disease," VCU Technology Transfer Marketing Flyer, as early as Apr. 12, 2007, available at www.research.vcu.edu/ott/licensable_technologies/flash/05-70_ward.htm, 2 pages.
Baig et al., "Comparison between Bed Side Testing of Blood Glucose by Glucometer vs Centralized Testing in a Tertiary Care Hospital," J. Ayub Med Coli Abbottabad vol. 19(3), 2007, 5 pages.
Bar-Or et al., "Heterogeneity and Oxidation Status of Commercial Human Albumin Preparations in Clinical Use," Critical Care Medicine, Jul. 2005, vol. 33, No. 7, pp. 1638-1641.
Bayir et al., "Assessment of Antioxidant Reserves and Oxidative Stress in Cerbrospinal Fluid after Severe Traumatic Brain Injury in Infants and Children," Pediatric Research, 2002, vol. 51(5), pp. 571-578.
Biffl et al., "Plasma from Aged Stored Red Blood Cells Delays Neutrophil Apoptosis and Primes for Cytotoxicity: Abrogation by Poststorage Washing but not Prestorage Leukoreduction," The Journal of Trauma, vol. 50, No. 3 (Mar. 2001), pp. 426-432, (Abstract) 1 page.
Brittingham et al., "Febrile Transfusion Reactions Caused by Sensitivity to Donor Leukocytes and Platelets," Journal of the American Medical Association, vol. 165, No. 7 (Oct. 19, 1957), pp. 819-825, (Abstract) 1 page.
Carballal et al., "Sulfenic Acid Formation in Human Serum Albumin by Hydrogen Peroxide and Peroxynitrite," Biochemistry, vol. 42 (2003), pp. 9906-9914.
Cases et al., "Response of antioxidant defences to oxidative stress induced by prolonged exercise: antioxidant enzyme gene expression in lymphocytes," European Journal of Applied Physiology, vol. 98, No. 3 (Oct. 2006), pp. 263-269.
Cernak et al. "Characterization of Plasma Magnesium Concentration and Oxidative Stress Following Graded Traumatic Brain Injury in Humans," Journal of Neurotrauma, Jan. 2000, vol. 17, No. 1, pp. 53-68.
Chevion et al., "Evaluation of Plasma Low Molecular Weight Antioxidant Capacity by Cyclic Voltammetry," Free Radical Biol. Med., 1997, vol. 22(3), pp. 411-421.
Chevion et al., "The Use of Cyclic Voltammetry for the Evaluation of Antioxidant Capacity," Free Radical Biol. Med., 2000, vol. 28(6), pp. 860-870.
Codd et al., "Redox Maintenance and Organ Preservation," Transplantation Proceedings, vol. 9, No. 3 (Sep. 1977), pp. 1569-1571, (Abstract) 1 page.
Codd et al., "Redox Maintenance in Restoration of Organ Viability," The Journal of Surgical Research, vol. 22, No. 5 (May 1977), pp. 585-592, (Abstract) 1 page.
Collins et al., "Optimal Redox Electrode Potential for 24-Hour Rabbit Kidney Perfusion," The Journal of Surgical Research, vol. 39, No. 3 (Sep. 1985), pp. 246-250, (Abstract) 1 page.
Cowley et al., Plasma antioxidant potential in severe sepsis: A comparison of survivors and nonsurvivors, Critical Care Medicine, vol. 24, No. 7 (Jul. 1996), pp. 1179-1183, available at www.ccmjournal.com/pt/re/ccm/fulltext.ooo03246-199607000-00019htm;jsessionid=F2GT . . . , 9 pages.
Dosek et al., "High Altitude and Oxidative Stress," Respiratory Physiology & Neurobiology, vol. 158, No. 2-3 (Sep. 30, 2007), pp. 128-131, (Abstract) 1 page.

EcoScan 5 & 6 Series, Economy Handheld, Eutech Instruments, May 16, 2007, 12 pages.
Elokda et al., "Effects of Exercise Training on the Gluthathione Antioxidant System," European journal of Cardiovascular Prevention and Rehabilitation : Official Journal of the European Society of Cardiology, Working Groups on Epidemiology & Prevention and Cardiac Rehabilitation and Exercise Physiology, vol. 14, No. 5 (Oct. 2007), pp. 630-637, (Abstract) 1 page.
Ernst et al., "Electrochemical characterisation of uric acid and ascorbic acid at a platinum electrode," Analytica Chimica Acta, 2001, vol. 449, pp. 129-134.
Ferretti et al., "Copper-induced Oxidative Damage on Astrocytes: Protective Effect Exerted by Human High Density Lipoproteins," Biochimica et biophysica acta, vol. 1635, No. 1 (Nov. 30, 2003), pp. 48-54 (Abstract) 1 page.
Ferretti et al,, "Paraoxonase Activity in High-Density Lipoproteins: A Comparison between Health and Obese Females," The Journal of Clinical Endocrinology & Metabolism, vol. 90, No. 3 (Mar. 2005), pp. 1728-1733.
Ferretti et al., "Protective Effect of Paroxonase Activity in High-density Lipoproteins Against Erythrocyte Membranes Peroxidation: A Comparison Between Healthy Subjects and Type 1 Diabetic Patients," The Journal of Clinical Endocrinology and Metabolism, vol. 89, No. 6 (Jun. 2004), pp. 2957-2962.
Fried et al., "Frailty in older adults: evidence for a phenotype," J. Gerontol A Biol Sci Med Sci., 2001, vol. 56(3), pp. M146-M156 (Abstract), 2 pages.
Galley et al., "Xanthine Oxidase Activity and Free Radical Generaton in Patients with Sepsis," Critical Care Medicine, vol. 24, No. 10 (Oct. 1996), pp. 1649-1653, (Abstract) 1 page.
Ghiselli et al., "Total Antioxidant Capacity as a Tool to Assess Redox Status: Critical View and Experimental Data," Free Radical Biology & Medicine, vol. 29, No. 11 (Dec. 2000), pp. 1106-1114, (Abstract) 1 page.
Gomez-Cabrera et al., "Moderate Exercise in an Antioxidant: Upregulation of Antioxidant genes by Training," Free Radical Biology & Medicine, vol. 44, No. 2 (Jan. 15, 2008), pp. 126-131, (Abstract) 1 page.
Goode et al., "Decreased Antioxidant Status and Increased Lipid Perosidation in Patients with Septic Shock and Secondary Organ Dysfunction," Critical Care Medicine, vol. 23, No. 4 (Apr. 1995), pp. 646-651, (Abstract) 1 page.
Green et al., "Effluent Redox Potential: A Rapid Method for Assaying Warm Ischemic Injury," The Journal of Surgical Research, vol. 25, No. 3 (Sep. 1978), pp. 222-225, (Abstract) 1 page.
Gubler et al. "Trauma Recidivism in the Elderly," The Journal of Trauma: Injury, Infection, and Critical Care, Dec. 1996, vol. 41, No. 6, pp. 952-956.
Horton, "Free Radicals and Lipid Peroxidation Mediated Injury in burn Trauma: The Role of Antioxidant Therapy," Toxicology, vol. 189, No. 1-2 (Jul. 15, 2003), pp. 75-88, (Abstract) 1 page.
Huang et al., "The Chemistry behind Antioxidant Capacity Assays," Journal of Agriculture and Food Chemistry, vol. 53 (2005), pp. 1841-1856.
Jellinek et al., "Electrochemical Control of Redox Potential in Perfusate for Prolonged Heart Storage," Transactions—American Society for Artificial Internal Organs, vol. 20 (1974), pp. B:533-537, (Abstract) 1 page.
Jellinek et al., "Oxidation-Reduction Maintenance in Organ Preservation," Archives of Surgery, vol. 120, No. 4 (Apr. 1985), pp. 439-442, (Abstract) 1 page.
Ji, "Antioxidants and Oxidative Stress in Exercise," Proceedings of the Society for Experimental Biology and Medicine, Society for Experimental Biology and Medicine (New York, N.Y.), vol. 222, No. 3 (Dec. 1999), pp. 283-292.
Ji, "Modulation of Skeletal Muscle Antioxidant Defense by Exercise: Role of Redox Signaling," Free Radical Biology & Medicine, vol. 44, No. 2, (Jan. 15, 2008), pp. 142-152 (Abstract) 1 page.
Kinumi, "Protein Modification due to Oxidative Stress," Sansouken Today, May 2006, vol. 6(5), pp. 28-29 (no English translation available).

(56) References Cited

OTHER PUBLICATIONS

Kohen et al., "Noninvasive in vivo evaluation of skin antioxidant activity and oxidation status," Methods in Enzymology, vol. 300 (1999), pp. 428-437.
Kohen et al., "Quantification of the overall reactive oxygen species scavenging capacity of biological fluids and tissues," Free Radical Biology & Medicine, vol. 28, No. 6 (Mar. 15, 2000), pp. 871-879.
Kyparos et al., "Short Duration Exhaustive Aerobic Exercise Induces Oxidative Stress: A Novel Play-oriented Volitional Fatigue Test," The Journal of Sports Medicine and Physical Fitness, vol. 47, No. 4 (Dec. 2007), pp. 483-490, (Abstract) 1 page.
Lamprecht et al., "Single Bouts of Exercise Affect Albumin Redox State and Carbonyl Groups on Plasma Protein of Trained Men in a Workload Dependent Manner," Journal of Applied Physiology, vol. 104, No. 6 (Jun. 2008), pp. 1611-1617, (Abstract) 1 page.
Lee et al., "A cobalt-coated needle-type microelectrode array sensor for in situ monitoring of phosphate," J. Micromech. Microeng., vol. 19, 2009, 2 pages, Abstract.
Lee et al., "Fabrication of microelectrode arrays for in situ sensing of oxidation reduction potentials," Sensors & Actuators B: Chem., vol. 115(1), May 23, 2006, 3 pages, Abstract.
Lekhi et al., "Influence of Exercise on Oxidant Stree Products in Elite Indian Cyclists," British Journal of Sports Medicine, vol. 41, No. 10 (Oct. 2007), pp. 691-693, (Abstract) 1 page.
Lemineur et al., "Biomarkers of oxidative stress in critically ill patients: What should be measured, when and how?" Curr. Opin. Clin. Nutr. Metabol. Care, Nov. 2006, vol. 9(6), pp. 704-710.
Margonis et al., "Oxidative Stress Biomarkers Responses to Physical Overtraining: Implications for Diagnosis," Free Radical Biology and Medicine, vol. 43, No. 6 (Sep. 15, 2007), pp. 901-910, (Abstract) 3 pages.
Mayer et al., "Reduced serum total reductive capacity in lethal severe trauma," The Journal of Trauma, vol. 51, No. 1 (Jul. 2001), pp. 88-91.
McAnulty et al., "Influence of Carbohydrate, Intense Exercise, and Rest Intervals on Homonal and Oxidative Changes," International Journal of Sport Nutrition and Exercise Metabolism, vol. 17, No. 5 (Oct. 2007), pp. 478-490, (Abstract) 1 page.
Meijer, "Exercise-induced oxidative stress in older adults as measure by antipyrine oxidation," Metabolism, vol. 50, No. 12 (Dec. 2001), pp. 1484-1488, (Abstract) 3 pages.
Michailidis et al., "Sampling Time is Critical for Measurement of Aerobic exercise-induced oxidative Stress," Medicine and Science in Sports and Exercise, vol. 39, No. 7 (Jul. 2007), pp. 1107-1113, (Abstract) 1 page.
Miller et al., "Acute Respiratory Distress Syndrome in Blunt Trauma: Identification of Independent Risk Factors," The American Surgeon, vol. 68, No. 10 (Oct. 2002), pp. 845-851, (Abstract) 1 page.
Miller et al., "Improved Myocardial Preservation by Control of the Oxidation-Reduction Potential," The Journal of Heart Transplantation, vol. 4, No. 3 (May 1985), pp. 319-324, (Abstract) 1 page.
Nikolaidis et al., "Decreased Blood Oxidative Stress After Repeated Muscle-Damaging Exercise," Medicine and Science in Sports and Exercise, vol. 39, No. 7 (Jul. 2007), pp. 1080-1089, (Abstract) 1 page.
Paschalis et al., "Uniform and Prolonged Changes in Blood Oxidative Stress After Muscle-damaging Exercise," In vivo (Athens, Greece), vol. 21, No. 5 (Sep.-Oct. 2007), pp. 877-883, (Abstract) 1 page.
Popov et al., "Photochemiluminescent detection of antiradical activity. VI. Antioxidant characeristics of human blook plasma, low density lipoprotein, serum albumin and amino acids during in vitro oxidation," Luminescence, vol. 14, 1999, pp. 169-174.
Popov et al., "Photochemiluminescent detection of antiradical activity. VII. Comparison with a modified method of thermo-initiated free radical generation with chemiluminescent detection," Luminescence, vol. 20, 2005, pp. 321-325.
Prasad et al., "Evaluation of oxidative stress after fractures. A preliminary study," Acta Orthopaedica Belgica, 2003, vol. 69(6), pp. 546-551.
Prior et al., "In Vivo Total Antioxident Capacity: Comparison of Different Analytical Methods," Free Radical Biology & Medicine, vol. 27, Nos. 11-12 (1999), pp. 1173-1181.
Prokhorov et al., "A method of redoxometry in clinical studies," Vopr. Med. Khim., vol. 35, No. 5 (Sep.-Oct. 1989), (includes English abstract) 6 pages.
Radak et al., "Effects of Exercise on Brain Function: Role of Free Radicals," Applied Physiology, Nutrition, and Metabolism, vol. 32, No. 5 (Oct. 2007), pp. 942-946, (Abstract) 1 page.
Radak et al., "Exercise, Oxidative Stress and Hormesis," Ageing Research Reviews, vol. 7, No. 1 (Jan. 2008), pp. 34-42, (Abstract) 1 page.
Radak et al., "Systemic Adaptation to Oxidative Challenge Induced by Regular Exercise," Free radical Biology & Medicine, vol. 44, No. 2 (Jan. 15, 2008), pp. 153-159, (Abstract) 1 page.
Rael et al., "Combined cupric-and cuprous-binding peptides are effective in preventing IL-8 release from endothelial cells and redox reactions," Biochemical and Biophysical Research Communications, vol. 357 (2007), pp. 543-548.
Rael et al., "Oxidation-reduction potential and paraxonase-arylesterase activity in trauma patients," Biochemical and Biophysical Research Communications, vol. 361 (2007), pp. 561-565.
Rael et al., "Plasma oxidation-reduction potential and protein oxidation in traumatic brain injury," J. Neurotrauma, Aug. 2009, vol. 26(8), pp. 1203-1211.
Rael et al., "The effect of storage on the accumulation of oxidative biomarkers in donated packed red blood cells," J. Trauma, Jan. 2009, vol. 66(1), pp. 76-81.
Rahnama et al., "Oxidative Stress responses in Physical Education Students During 8 Weeks Aerobic Training," The Journal of Sports Medicine and Physical Fitness, vol. 47, No. 1 (Mar. 2007), pp. 119-123, (Abstract) 1 page.
Rana et al., "Study on Oxidative Stress in Patients with Abdominal Trauma," Molecular and Cellular Biochemistry, vol. 291, No. 1-2 (Oct. 2006), pp. 161-166, (Abstract) 1 page.
Rao et al., "Redox Potential Measurements of Plasma in Patients Undergoing Coronary Artery Bypass Graft and Its Clinical Significance," Journal of Pharmacological and Toxicological Methods, vol. 38 (1997), pp. 151-156.
Rice-Evans, "Measurement of Total Antioxidant Activity as a Marker of Antioxidant Status in Vivo: Procedures and Limitations," Free Radical Research, vol. 33, Supplement (Nov. 2000), pp. 59-66, (Abstract) 1 page.
Rosenberg et al. "Who bounces back? Physiologic and other predictors of intensive care unit readmission," Critical Care Medicine, Mar. 2001, vol. 29, No. 3, pp. 511-518.
Roth et al., "Assessing the antioxidative status in critically ill patients," Current Opinion in Clinical Nutrition and Metabolic Care, vol. 7 (2004), pp. 161-168.
Reuter et al., "Oxidative stress, inflammation, and cancer: How are they linked?" Free Radical Biol. Med., 2010, vol. 49(11), pp. 1603-1616 [doi:10.1016/j.freeradbiomed.2019.09.06], 40 pages.
Sauaia et al., "Early Predictors of Postinjury Multiple Organ Failure," Archives of Surgery, vol. 129, No. 1 (Jan. 1994), pp. 39-45, (Abstract) 1 page.
Sen et al., "Antioxidants in Exercise Nutrition," Sports Medicine (Auckland, N.Z.), vol. 31, No. 13 (2001), pp. 891-898, (Abstract) 1 page.
Shin et al., "Exercise Training Improves the Antioxidant Enzyme Activity with no Change of Telomere Length," Mechanisms of Ageing and Development, vol. 129, No. 5 (May 2008), pp. 254-260, (Abstract) 1 page.
Shing et al., "The Effect of Consecutive Days of Exercise on Markers of Oxidative Stress," Applied Physiology, Nutrition, and Metabolism, vol. 32, No. 4 (Aug. 2007), pp. 677-685, (Abstract) 1 page.
Siesjo et al., "Free radicals and brain damage," Cerebrovasc Brain Metab Rev, 1989, vol. 1(3), pp. 165-211 (Abstract), 1 page.
Soffler, "Oxidative Stress," The Veterinary Clinics of North America. Equine Practice, vol. 23, No. 1 (May 2007), pp. 135-157 (Abstract) 1 page.

(56) References Cited

OTHER PUBLICATIONS

Steinberg et al., "Cytokine and Oxidative responses to Maximal Cycling Exercise in Sedentary Subjects," Medicine and Science in Sports and Exercise, vol. 39, No. 6 (Jun. 2007), pp. 964-968, (Abstract) 1 page.

Turk et al., "Promotion of Fracture Healing by Vitamin E in Rats," Journal of International Medical Research, 2004, vol. 32(5), pp. 507-512.

Veglia et al., "Age- and gender-related oxidative status determined in healthy subjects by means of OXY-SCORE, a potential new comprehensive index," Biomarkers, vol. 11, No. 6 (Nov.-Dec. 2006), pp. 562-573.

Vollard et al., "Exercise-induced oxidative stress: Myths, realities and physiological relevance," Sports Med., 2005, vol. 35(12), pp. 1045-1062.

Williams et al., "Dietary Supplements and Sports Performance: Introduction and Vitamins," Journal of the International Society of Sports Nutrition, vol. 1, No. 2 (2004), pp. 1-6.

Winterbourn et al., "Protein Carbonyl Measurements Show Evidence of Early Oxidative Stress in Critically Ill Pateints," Critical Care Medicine, vol. 28, No. 1 (Jan. 2000), pp. 275-277 (Abstract) 1 page.

Yeler et al., "Investigation of oxidative stress during fracture healing in the rats," Cell Biochemistry and Function, 2005, vol. 23(2), pp. 137-139.

Yu et al., "Stratification and Oxidation-Reduction Potential Change in an Aerobic and Sulfate-Reducing Biofilm Studied Using Microelectrodes," JSTOR: Water Environment Research, vol. 73, No. 3, May-Jun. 2001, 2 pages, Abstract.

Zoppi et al., "Overreaching-induced oxidative stress, enhanced HSP72 expression, antioxidant and oxidative enymes downregulaltion," Scandinavian Journal of Medicine & Science in Sports, vol. 18, No. 1 (Feb. 2008), pp. 67-76 (Abstract) 3 pages.

Written Opinion for International (PCT) Patent Application No. PCT/US08/63855, mailed Aug. 26, 2008, 8 pages.

International Search Report for International (PCT) Patent Application No. PCT/US08/63855, mailed Aug. 26, 2008, 3 pages.

International Preliminary Report on Patentability for International (PCT) Patent Application No. PCT/US08/63855, mailed Nov. 24, 2009, 10 pages.

Extended European Search Report for European Patent Application No. 08755661.9, dated Aug. 3, 2010, 7 pages.

International Search Report for International (PCT) Patent Application No. PCT/US2012/026884, mailed Jun. 21, 2012 4 pages.

Written Opinion for International (PCT) Patent Application No. PCT/US2012/026884, mailed Jun. 21, 2012 6 pages.

International Preliminary Report on Patentability for International (PCT) Patent Application No. PCT/US2012/026884, mailed Sep. 3, 2013 8 pages.

International Search Report and Written Opinion for International Patent Application No. PCT/US13/37357, mailed Aug. 26, 2013, 10 pages.

Ridley "The recognition and early management of critical illness," Annals of the Royal College of Surgeons of England, Sep. 2005, vol. 87, No. 5, pp. 315-322.

Senior et al., "Effect of Revascularization on Left Ventricular Remodeling in Patients With Heart Failure from Severe Chronic Ischemic Left Ventricular Dysfunction," Am. J. Cardiology, 2001, vol. 88(6), pp. 624-629.

Shohami et al. "Oxidative Stress in Closed-Head Injury: Brain Antioxidant Capacity as an Indicator of Functional Outcome," Journal of Cerebral Blood Flow and Metabolism, Oct. 1997, vol. 17, No. 10, pp. 1007-1019.

\* cited by examiner

METHODS AND SYSTEMS FOR MEASURING AND USING THE OXIDATION-REDUCTION POTENTIAL OF A BIOLOGICAL SAMPLE

CROSS-REFERENCE TO RELATED APPLICATIONS

This application claims the benefit of U.S. Provisional Patent Application Ser. No. 61/717,511, filed Oct. 23, 2012, and U.S. Provisional Patent Application Ser. No. 61/868,983, filed Aug. 22, 2013, the entire disclosures of which are hereby incorporated herein by reference.

FIELD

The present invention relates to methods and apparatuses for measuring the oxidation-reduction potential of a fluid sample and methods of using the same.

BACKGROUND

Whole blood and blood products, such as plasma and serum, have oxidation-reduction potentials (ORP). Clinically the ORP of blood, plasma and serum provides the oxidative status of an animal. More particularly, the ORP of blood, plasma and serum is related to health and disease.

An oxidation-reduction system, or redox system, involves the transfer of electrons from a reductant to an oxidant according to the following equation:

  (1)

where ne⁻ equals the number of electrons transferred. At equilibrium, the redox potential (E), or oxidation-reduction potential (ORP), is calculated according to the Nernst-Peters equation:

$$E(ORP)=E_o-RT/nF \ln [\text{reductant}]/[\text{oxidant}] \quad (2)$$

where R (gas constant), T (temperature in degrees Kelvin) and F (Faraday constant) are constants. $E_o$ is the standard potential of a redox system measured with respect to a hydrogen electrode, which is arbitrarily assigned an $E_o$ of 0 volts, and n is the number of electrons transferred. Therefore, ORP is dependent on the total concentrations of reductants and oxidants, and ORP is an integrated measure of the balance between total oxidants and reductants in a particular system. As such, ORP provides a measure of the overall oxidative status of a body fluid or tissue of a patient.

Oxidative stress is caused by a higher production of reactive oxygen and reactive nitrogen species or a decrease in endogenous protective antioxidative capacity. Oxidative stress has been related to various diseases and aging, and it has been found to occur in all types of critical illnesses. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. Several investigations have shown a close association between the oxidative status of a critically ill patient and the patient's outcome. See Roth et al., *Current Opinion in Clinical Nutrition and Metabolic Care*, 7:161-168 (2004).

Oxidative stress in patients has been evaluated by measuring various individual markers. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. However, such measurements are often unreliable and provide conflicting and variable measurements of the oxidative status of a patient. See Veglia et al., *Biomarkers*, 11(6): 562-573 (2006); Roth et al., *Current Opinion in Clinical Nutrition and Metabolic Care*, 7:161-168 (2004). The measurement of multiple markers which are then used to provide a score or other assessment of the overall oxidative status of a patient has been developed to overcome the problems of using measurements of single markers. See Veglia et al., *Biomarkers*, 11(6): 562-573 (2006); Roth et al., *Current Opinion in Clinical Nutrition and Metabolic Care*, 7:161-168 (2004). Although such approaches are more reliable and sensitive than measurements of a single marker, they are complex and time consuming. Thus, there is a need for a simpler and faster method for reliably measuring the overall oxidative status of a patient.

The oxidation/reduction potential can be measured electrochemically. Electrochemical devices for measuring ORP of blood and blood products typically require large sample volumes (that is, ten to hundreds of milliliters) and long equilibrium periods. Furthermore, the electrochemical devices have large, bulky electrodes that require cleaning between sample measurements. Such electrochemical devices are poorly suited for routine clinical diagnostic testing. It has been suggested to use electrodes that have undergone treatment to prevent biofouling. However, such devices necessarily involve complex manufacturing techniques. Moreover, conventional electrochemical devices have not provided a format that is convenient for use in a clinical setting.

The oxidative and radical characteristics of human blood plasma and its blood components (such as low density lipoproteins, serum albumin, and amino acids) can also be determined from photo chemiluminescence, with and without thermo-initiated free radical generation. A photo chemiluminescent system generally includes a free radical generator and a detector that measures chemiluminometric changes in the presence of an antioxidant. More specifically, the blood plasma sample (or one of its components) containing an amount of antioxidant is contacted and reacted with a known amount of free radicals. The free radicals remaining after contacting the blood plasma sample are determined chemiluminometrically. This type of measurement and detection system is not suitable for rapid, large scale measurements of blood plasma samples in a clinical setting for assessing or monitoring human or animal health.

There remains a need for improved methods and devices for measuring the oxidation-reduction characteristics of biological samples. Further, there is a need for use of such improved methods and devices in novel applications.

SUMMARY

Embodiments of the present invention are directed to solving these and other problems and disadvantages of the prior art, and provide systems and methods for measuring oxidation-reduction potential (ORP) characteristics (i.e., static oxidation-reduction potential (sORP) and/or the oxidation-reduction potential capacity (cORP)) of a fluid. Moreover, the measured ORP can provide information regarding the status of a subject rapidly and conveniently in a clinical and/or emergent setting.

Systems in accordance with embodiments of the present disclosure generally include a test strip with a reference cell, a sample chamber, and a plurality of electrodes. The sample chamber is configured to receive a fluid sample. The system additionally includes a readout device with contacts for interconnection to the electrodes of a test strip, a test signal power supply, and an electrometer. The readout device can additionally include memory and a processor operable to execute programming code stored in the memory to operate the power supply and record a voltage sensed by the electrometer over time.

More particularly, a system for identifying an oxidative capacity of a fluid in accordance with embodiments of the present disclosure can include:
   a fluid sample;
   a test strip, including:
   a reference cell;
   a sample chamber;
   a counter electrode, wherein a first portion of the counter electrode extends into the sample chamber;
   a working electrode, wherein a first portion of the working electrode extends into the sample chamber;
   a reference electrode, wherein the reference electrode is in electrical contact with the reference cell;
   a readout device, including:
   a first contact;
   a second contact;
   a third contact;
   a test signal power supply, wherein a first terminal of the test signal power supply is electrically connected to the first contact, and wherein a second terminal of the test signal power supply is electrically connected to the second contact;
   an electrometer, wherein a first input of the electrometer is electrically connected to the second contact, and wherein a second input of the electrometer is electrically connected to the third contact;
   memory;
   a processor, wherein with the first contact electrically connected to the counter electrode, the second contact electrically connected to the working electrode, and the third contact electrically connected to the reference electrode, and with the fluid sample in the sample chamber, the processor is operable to execute programming code stored in the memory to:
   operate the test signal power supply to supply a current across the sample chamber between the counter electrode and the working electrode for at least a first period of time;
   during the first period of time, monitor the voltage sensed by the electrometer;
   identify an inflection point in the voltage sensed by the electrometer;
   record the time at which the inflection point is identified.

The processor can also operate to integrate the current between a start time and the time at which the inflection point is reached to obtain an oxidation-reduction capacity of the fluid sample. Alternatively or in addition, the processor can operate the test signal power supply to supply the current at a static first level for a first time segment, and after the first time segment, operate the test signal power supply to supply the current at a rising level for at least a second time segment.

The system can additionally include a readout device incorporating an output device, wherein the obtained oxidation-reduction capacity of the fluid sample is output to a user by the output device. The output can be provided in units of Coulombs$^{-1}$.

Methods in accordance with embodiments of the present disclosure include techniques for obtaining ORP characteristics of a fluid sample. The disclosed methods include applying a current to a fluid sample, and measuring a voltage across that fluid sample over a period of time while the current is applied. An inflection or transition point, such as a point at which the voltage is changing the fastest, can be identified. The quantity of current applied between the first period of time and the inflection point can then be integrated to obtain a value with units of Coulombs that is indicative of an oxidation-reduction capacity of the fluid sample. The determined value can then be output, for example for diagnostic or other purposes.

In accordance with embodiments of the present disclosure, a method for measuring oxidation-reduction potential capacity is disclosed that includes:
   applying a current to a fluid sample;
   measuring a voltage across the fluid sample over a first period of time, while applying the current to the fluid sample;
   integrating the applied current over the first period of time to obtain a value indicative of an oxidation reduction capacity.

The current can be applied to the fluid sample between a counter electrode and a working electrode, and the voltage across the fluid sample can be measured between a reference electrode and the working electrode.

In accordance with at least some embodiments of the method, the current applied to the fluid sample is varied over time.

The inflection point in the measured voltage can be identified. In addition, the first period of time over which the current is integrated can end at a time at which the inflection point is identified.

The current can be held constant during at least a first segment of the first period of time, and the current can be varied during at least a second segment of the first period of time. The first segment of the first period of time can follow the second segment of the first period of time. Moreover, the current can be increased at a linear rate during the second segment of the first period of time. Alternatively, the current can be increased at an exponential rate during the second segment of the first period of time. As yet another alternative, the current can be increased according to a step function during the second segment of the first period of time.

According to at least some embodiments, the inflection point is the point at which the rate of change in the measured voltage is at a local maximum.

In accordance with still other embodiments, a readout device is provided that includes a plurality of readout contacts, and an analog front end. The analog front end includes a current supply and an electrometer. The current supply is operable to provide a current to first and second contacts of the plurality of readout contacts. The electrometer is operable to read a voltage potential between the second contact and the third contact of the readout contacts.

The readout device can further include a controller and an analog to digital converter that connects the electrometer to the controller. In addition, the readout device can include a digital to analog converter that connects the controller to the current supply.

The controller can operate to determine an inflection point in the voltage potential, and to determine a quantity of charge supplied between a first time and the inflection point.

A user interface can be provided that includes a user output. The user output can provide an oxidation reduction potential capacity value that is derived from the determined quantity of the charge supplied between the first time and the inflection point.

A connector that is operative to receive a test strip containing a fluid sample can also be included in the readout device. The connector includes the readout contacts, and places the readout contacts in operative contact with leads of the test strip.

Additional features and advantages of embodiments of the present disclosure will become more readily apparent from the following detailed description, particularly when taken together with the accompanying drawings.

DETAILED DESCRIPTION

Figure 1:
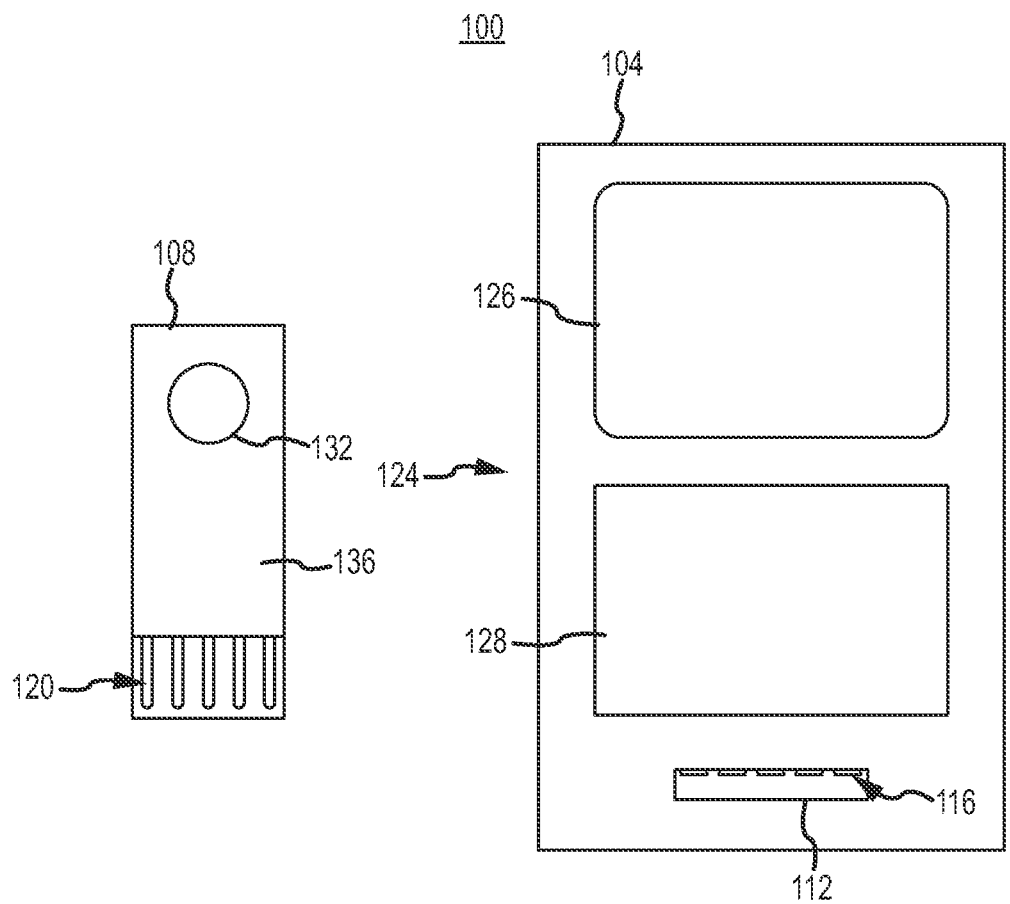
FIG. 1 depicts components of a system for measuring the oxidation-reduction potential capacity of a fluid in accordance with embodiments of the present invention.

Embodiments of the present invention provide systems and methods for measuring oxidation-reduction potential (ORP) characteristics (i.e., static oxidation-reduction potential (sORP) and/or oxidation-reduction capacity (cORP)) of a fluid that are suitable for rapid, routine clinical diagnostic testing and methods of using the system to evaluate or monitor the status of a subject. The system generally includes a test strip and a readout device. More particularly, embodiments of the present invention can determine the ORP characteristics of a body fluid of a patient in a convenient and timely manner. A biological sample of a patient that can be used in the method of invention can be any body fluid. Suitable body fluids include a blood sample (e.g., whole blood, serum or plasma), urine, saliva, cerebrospinal fluid, tears, semen, vaginal secretions, amniotic fluid and cord blood. Also, lavages, tissue homogenates and cell lysates can be utilized and, as used herein, "body fluid" includes such preparations. Preferably, the body fluid is blood, plasma, serum or cerebrospinal fluid. For head injuries, the body fluid is most preferably cerebrospinal fluid or plasma. In cases other than head injuries, the body fluid is most preferably plasma.

The test strip generally includes a substrate, a reference cell, a counter electrode, a working electrode, a reference electrode, and a sample chamber. In general, by placing a fluid sample in the sample chamber, an electrical connection is established between the reference cell, the counter electrode, the working electrode, and the reference electrode. The test strip can then be connected to a readout device, for the determination of a static ORP value and an ORP capacity value.

The readout device generally includes contacts to electrically interconnect the readout device to the various electrodes included in the test strip. In accordance with embodiments of the present disclosure, the readout device includes an analog front end. The analog front end generally functions to provide a controlled current that can be sent across the fluid in the sample chamber through an electrical connection to the counter electrode and the working electrode. In addition, the analog front end is operable to generate a voltage signal that represents the potential difference between the reference electrode and the working electrode. An analog to digital (ADC) converter is provided to convert the voltage signal representing the reference electrode to working electrode potential difference to a digital signal. A digital to analog converter (DAC) is provided to convert a digital control signal to analog signals in connection with the provision of the controlled current to the test strip. A controller interfaces with the ADC and the DAC. Moreover, the controller can include or comprise a processor that implements programming code controlling various functions of the readout device, including but not limited to controlling the current supply to the test strip, and processing the potential difference measurement signal. The controller can operate in association with memory. In addition, the readout device includes a user interface, and a power supply.

FIG. 1 depicts components of a system 100 for measuring the oxidation-reduction potential (ORP) value, including but not limited to the static oxidation-reduction value (sORP) and/or the oxidation-reduction capacity value (cORP), of a fluid sample in accordance with embodiments of the present disclosure. As used herein, the sORP is a measured potential difference or voltage across a fluid sample such as a measured potential difference or voltage across a fluid sample placed in a test strip that includes a reference cell as described herein. The cORP as used herein is a measure of the quantity of charge provided to a fluid sample over a defined period such as can be measured in a test strip as described herein. Accordingly, the cORP can be viewed as the capacity of a fluid sample to absorb an electrical charge supplied as a current over some defined period. For example, the period can be defined by a start point corresponding to the initiation of current supply to a sample and an endpoint such as an inflection point or a midpoint between a first and a second inflection point. In general, the system 100 includes a readout device 104, which can implement a galvanometer, and a test strip 108. The readout device 104 includes a connector or readout aperture 112 for electrically interconnecting readout contacts 116 of the readout device 104 to electrode contacts 120 provided as part of the test strip 108. The readout device 104 can also incorporate a user interface 124, which can include a user output 126, such as a display, and a user input 128, such as a keypad. In accordance with still other embodiments, the user interface 124 can comprise an integrated component, such as a touch screen interface. In addition to providing contacts 120 for interconnecting the test strip 108 to the readout device 104, the test strip 108 includes a sample chamber aperture 132 formed in a test strip overlay 136, to receive a fluid sample in connection with the determination of an ORP value of that fluid sample.

Figure 2:
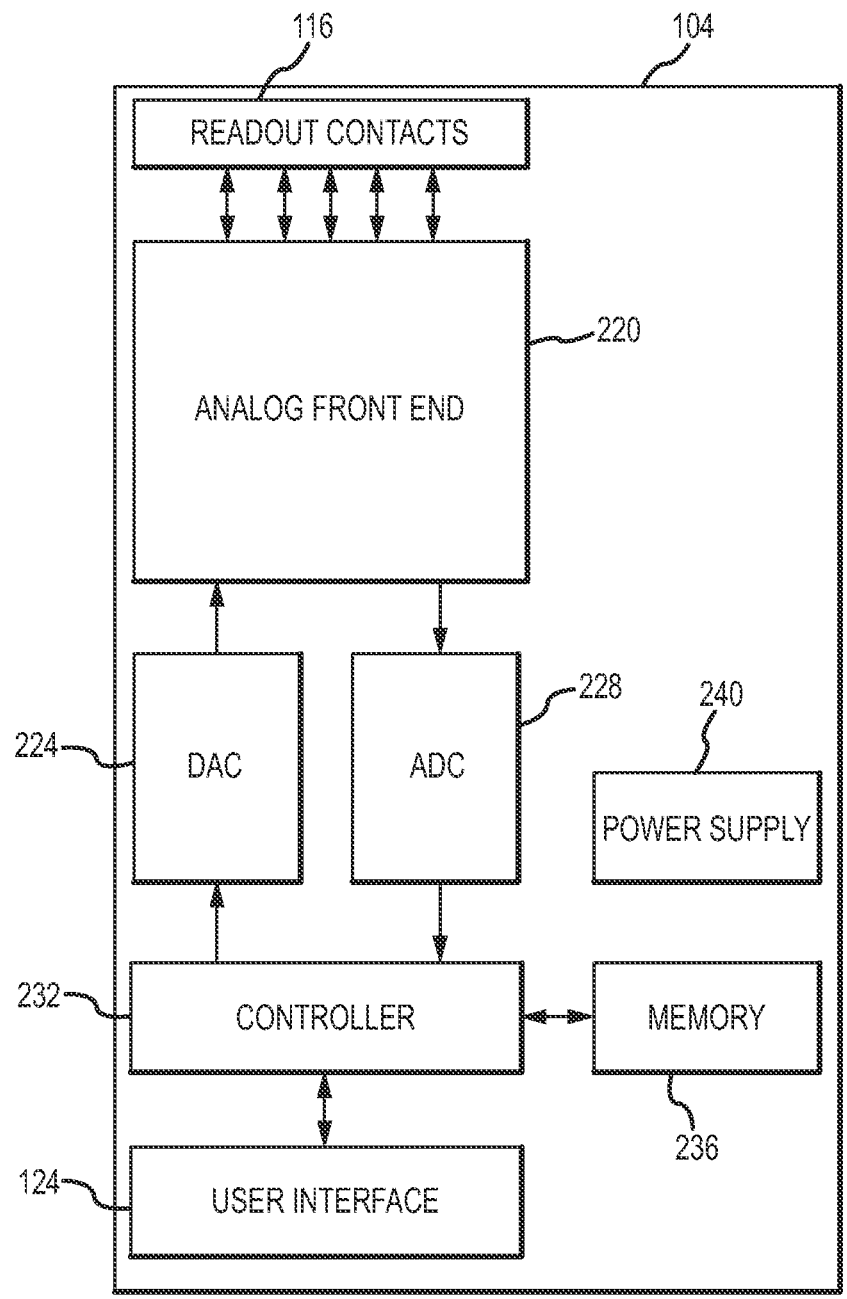
FIG. 2 illustrates components of a readout device in accordance with embodiments of the present disclosure.

FIG. 2 illustrates additional components and features of a readout device 104 in accordance with embodiments of the present disclosure. As shown, the readout contacts 116 are interconnected to an analog front end 220. As described in greater detail elsewhere herein, the analog front end 220 generally functions to provide a controlled current that is passed between a counter electrode and a working electrode of the test strip 108. In addition, the analog front end 220 functions to provide a voltage signal representing a potential difference between a reference electrode and the working electrode of the test strip 108. In accordance with still further embodiments, the analog front end 220 can include a strip detect circuit, to provide a signal indicating the interconnection of a test strip 108 to the readout device 104.

The analog front end 220 generally receives control signals from a digital to analog (DAC) converter 224. Signals output by the analog front end 220 are generally provided to an analog to digital converter (ADC) 228. The DAC 224 and ADC 228 are in turn connected to a controller 232. The controller 232 may comprise a processor that is operable to execute instructions stored in memory as part of the controller 232, or as a separate memory device 236. For example, the processor, executing instructions stored in memory 236, can implement a process according to which the current supplied to the test strip 108 is controlled. In addition, the controller 232 can execute instructions stored in memory 236 to record the quantity of current supplied to the test strip 108, to detect an inflection point in the voltage potential between electrodes of the test strip 108, and to calculate an ORP capacity. The memory 236 can also function as storage for data, including but not limited to intermediate and/or final ORP values. The controller 232, for example, can comprise a general purpose programmable processor or controller or a specially configured application integrated circuit (ASIC).

The user interface 124 generally operates to provide user input to the controller 232. In addition, the user interface 124 can operate to display information to a user, including but not limited to the status of the readout device 104 or of the system 100 generally, a sORP value, and a cORP value.

The readout device 104 also generally includes a power supply 240. Although not shown in the figure, the power supply 240 is generally interconnected to power consuming devices via a power supply bus. The power supply 240 may be associated with a battery or other energy storage device, and/or line power.

Figure 3:
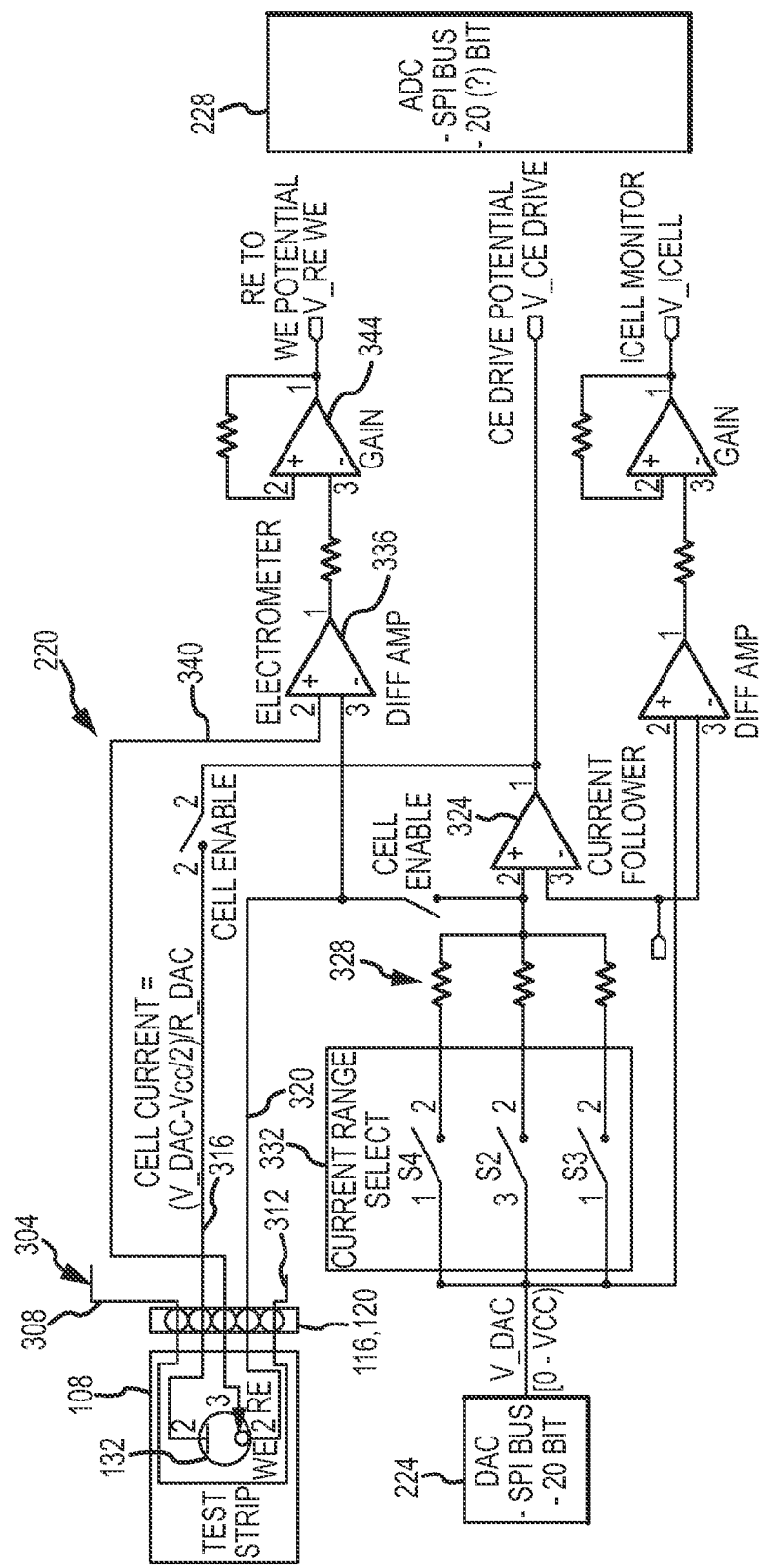
FIG. 3 illustrates further aspects of a readout device in accordance with embodiments of the present disclosure.

With reference now to FIG. 3, additional features of a system 100 in accordance with embodiments of the present disclosure are depicted. More particularly, details of the analog front end 220 and of the electrical circuit associated with the test strip 108 are depicted. As shown, the readout contacts 116 interconnect to the electrode leads or contacts 120, to electrically connect the analog front end 220 to the test strip 108. In the illustrated embodiment, the analog front end 220 includes a test strip sense circuit 304. The test strip sense circuit 304 includes a test strip detection supply lead 308 and a test strip detection input lead 312. In general, when a suitable test strip 108 is operatively connected to the readout device 104, continuity between the test strip detect supply lead 308 and the test strip detection input lead 312 is established, allowing a test strip detect signal indicating that a test strip 108 is present to be passed between the supply 308 and the input 312 leads. Moreover, a test strip 108 can incorporate a resistor or other component to modify the test strip detect signal, to indicate to the readout device 104 characteristics of the particular test strip 108 that has been interconnected to the readout device 104, such as the voltage value of a reference cell incorporated into the test strip 108. In response to sensing the presence of a test strip 108, the readout device 104 can operate to provide an interrogation signal in the form of a controlled current to the test strip 108.

The current is provided by the readout device 104 to the sample chamber 132 of the test strip 108 via a counter electrode lead 316 and a working electrode lead 320. More particularly, the current may be supplied to the counter electrode lead 316 from the output of a current follower 324, while the working electrode 320 can be provided as an input to that current follower 324. In addition, a set of current range select resistors 328 and associated switches 332 can be controlled by the DAC 224, as directed by the controller 232, for example depending on the characteristics of the interconnected test strip 108. In addition, the DAC 224, as directed by the controller 232, can control the input to the current follower 324 to in turn control the amount of current supplied to the test strip 108 by the current electrode lead 316. The DAC 224, as directed by the controller 232, can also operate various switches and/or amplifiers to control the operating mode of the analog front end 220.

The analog front end 220 additionally includes an electrometer 336 that receives a first input signal from a reference electrode lead 340 and a second input signal from the working electrode lead 320. The output from the electrometer 336 generally represents the potential difference between the reference electrode lead 340 and the working electrode lead 320. The signal output by the electrometer 336 can be amplified in a gain circuit 344, and output to the ADC 228.

Figure 4:
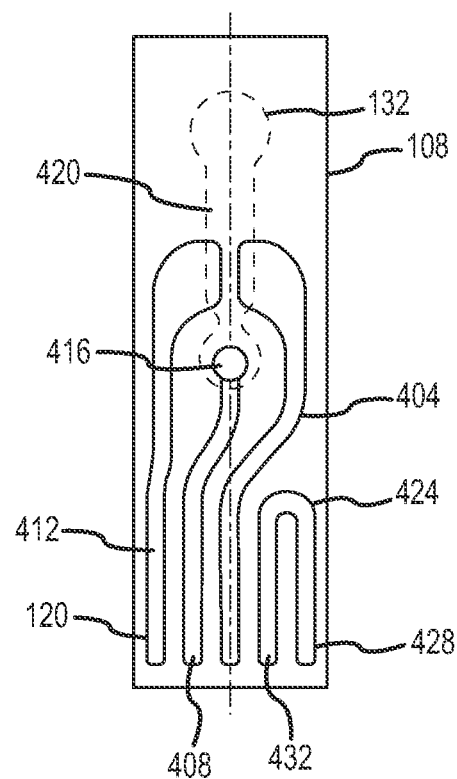
FIG. 4 depicts a test strip in accordance with embodiments of the present invention.

FIG. 4 depicts aspects of a test strip 108 in accordance with embodiments of the present invention. More particularly, the view presented by FIG. 4 shows the test strip 108 with the test strip overlay 136 removed. In general, the test strip 108 includes a working electrode 404, a reference electrode 408, and a counter electrode 412. In addition, the test strip 108 includes a reference cell 416. By placing a fluid sample within a sample chamber region 420, the working electrode 404, the reference electrode 408, the counter electrode 412, and the reference cell 416 are placed in electrical contact with one another. Moreover, by placing the electrode contacts 120 corresponding to the counter electrode 412, the working electrode 404 and the reference electrode 408 in contact with the readout contacts 116 corresponding to the counter electrode lead 316, the working electrode lead 320, and the reference electrode lead 340 respectively, the test strip 108 is operatively connected to the readout device 104. Accordingly, a supply current provided to the test strip 104 can be sent across the fluid sample, between the counter electrode 412 and the working electrode 404 by the readout device 104. Moreover, the potential difference between the reference electrode 408 and the working electrode 404 can be sensed by the readout device 104. In accordance with further embodiments of the present disclosure, the test strip 108 can include a test strip detect circuit 424, that includes an input 428 and an output 432. The test strip detect circuit 424 can, in addition to the input 428 and the output 432, include a resistor or other component for modifying a test strip sense signal provided by the readout device 104, to indicate to the readout device 104 an identification of the test strip 108.

To measure the cORP or antioxidant reserve, the sample is titrated with a linearly increasing oxidizing current between a counter and working electrode to exhaust the relevant antioxidants at the working electrode while monitoring the voltage between the working and reference electrodes. The result is a time vs voltage curve and a time vs current curve. The time versus voltage curve is used to find an inflection point where the voltage is changing the fastest (antioxidants are exhausted so system tries to find a new equilibrium). The time at maximum velocity (i.e., at the inflection point) is referred to as the transition time. The capacity or cORP is then the integral of the current profile from the beginning to the transition time with units of uC.

Calculation of the transition time may be accomplished several ways including noise filtration, curve fitting and standard numerical differentiation techniques. Usually the unfiltered numerical derivative is noisy, making finding maxima difficult or unreliable. To that end one technique is to curve fit the time versus voltage profile with a polynomial (5th-7th order is usually sufficient) and directly differentiating the resulting polynomial analytically. This approach has the advantage of very smooth derivatives making the determination of the transition time robust as long as the fit is good.

Figure 5:
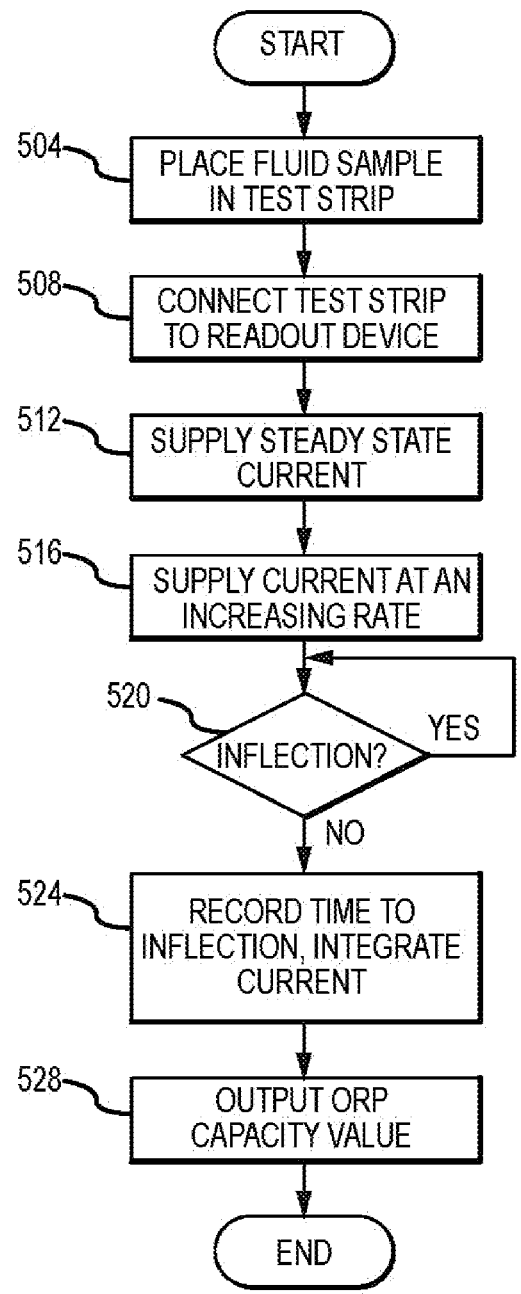
FIG. 5 is a flowchart depicting aspects of a method for measuring oxidation-reduction potential capacity in accordance with embodiments of the present disclosure.

FIG. 5 is a flowchart illustrating aspects of the operation of a system 100 for determining the ORP, including but not limited to the cORP, of a fluid sample in accordance with embodiments of the present invention. In general, the method includes obtaining a fluid sample and placing the fluid sample in the sample chamber 420 of a test strip 108 (step 504). At step 508, the test strip 108 is connected to the readout device 104 (step 508). In general, while the readout device 104 is in an on or standby mode, an electrical signal may be output by the test strip detection output lead 308. By connecting a suitable test strip 108 to a readout device 104, continuity between the test strip detect output lead 308 and the test strip detect input lead 312 is established. In addition, the signal received at the test strip detect input lead 312 can provide an indication of characteristics of the test strip 108, which can in turn be used to control aspects (e.g., a current range) of a current supplied to the test strip 108. Such characteristics can include but are not limited to the type and composition of the test strip electrodes 404, 408 and 412, and the potential of the reference cell 416.

At step 512, a current can be supplied by the readout device 104 to the counter electrode 412 of the test strip 108. More particularly, a current can be passed between the counter electrode 412 and the working electrode 404 by the counter electrode lead 316 and the working electrode lead 320. In accordance with embodiments of the present disclosure, the current that is supplied to the test strip 108 is controlled by the controller 232 of the readout device 104. More particularly, the current can be provided for at least a first segment of time at a selected, steady state level. The first segment of time can be a fixed time period. Alternatively, the first segment of time can expire once a determination has been made that the potential difference sensed by the readout device 104 between the reference electrode 408 and the working electrode 404 has a rate of change that is less than some selected amount. In accordance with still other embodiments, a combination of parameters may be applied to determine the time period over which the current is supplied at a steady state. Moreover, in accordance with other embodiments, no current is supplied during the first period of time (i.e. the supplied current during the first segment of time is zero). As can be appreciated by one of skill in the art after consideration of the present disclosure, while no current is supplied and while the rate of change of that potential difference is zero or less than some selected amount, the potential difference measured by the readout device 104 between the reference electrode 408 and the working electrode 404 is equal to the sORP of the fluid sample.

After the first segment of time has expired, the current can be supplied at an increasing rate (step 516). For example, the amount can be increased linearly, as a step function, exponentially, according to a combination of different profiles, or in any other fashion. For instance, the current can be increased linearly from 0 amps at a specified rate until an endpoint is reached. As another example, the amount can be stepped from 0 amps to some non-zero value, and that non-zero value can be provided at a steady rate for some period of time, or can be provided at an increasing rate according to some function. At step 520, a determination can be made as to whether an inflection point in the potential difference monitored between the reference electrode 408 and the working electrode 404 has been detected. More particularly, the reference electrode lead 340 and the working electrode lead 320 connect the reference electrode 408 and the working electrode 404 respectively to the electrometer 336, which outputs a signal representing the potential difference between the reference 408 and the working 404 electrodes. The analog to digital converter 228 then converts the signal representing the potential difference between the reference 408 and working 404 electrodes to a digital signal that is provided to the controller 232. If an inflection point has been detected, the readout device 104, and in particular the controller 232, can record the time from which current was first supplied to the time at which the inflection point is reached. In addition, the controller 232 can integrate the current signal to determine an amount of charge that has been supplied to the fluid sample up to the time at which the inflection point is reached (step 524).

In accordance with embodiments of the present disclosure, a first inflection point (e.g., a point at which the voltage measured across a fluid sample while a current is being supplied is at a local maximum rate of change) is used as the point at which integration of the current is stopped. However, multiple inflection points can be observed in the measured voltage. Accordingly, rather than using the first observed inflection point as the end point for integration, a subsequent inflection point can be used. As yet another example, a time determined with reference to multiple inflection points, such as a midpoint between two observed inflection points or an average time of multiple observed inflection points can be used as the end point of the integration for purposes of determining the cORP of a fluid sample. At step 528, the determined quantity of charge or a value derived from the determined quantity of charge can be output to a user as an ORP capacity (cORP) value for the fluid sample, for example through the output device 128 facility of a user interface 124 provided as part of or interconnected to a readout device 104. For example, the cORP value can be defined as one over the quantity of charge. The process can then end.

Figure 6:
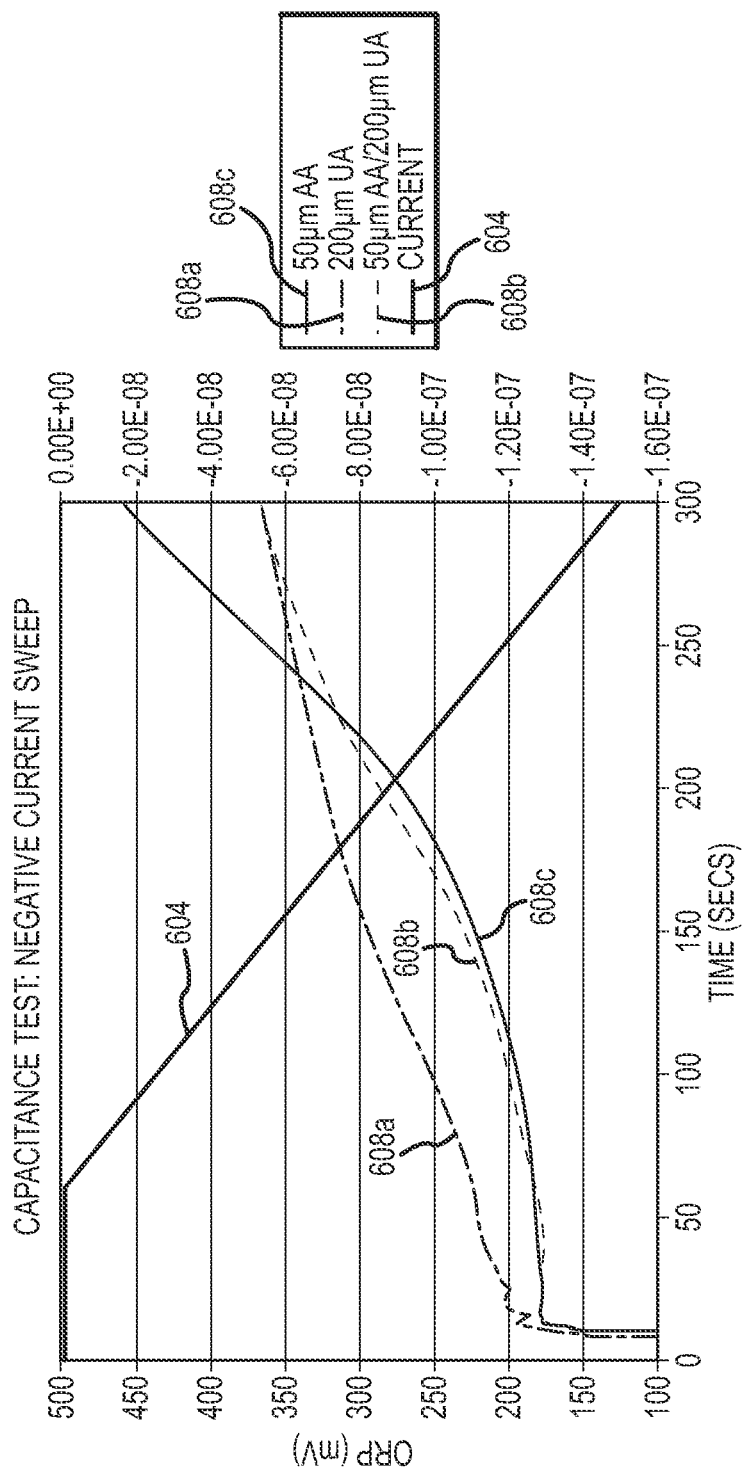
FIG. 6 is a graph depicting a supplied current and a measured potential difference over time.

FIG. 6 depicts the current, shown as line 604, supplied by a readout device 104 to an interconnected test strip 108 over time. In addition, sample measured potential difference values 608*a*-*c* for different exemplary samples are depicted. As can be understood by one of skill in the art after consideration of the present disclosure, although three potential difference values 608 are shown, a current 604 is provided to only one fluid sample during determination of an ORP value. As can also be appreciated by one of skill in the art after consideration of the present disclosure, the ramped portion of the current 604 is shown sloping in a downward direction, because it depicts an oxidizing current. In addition, it can be appreciated that the area between the current curve 604 and a current value of zero for a selected period of time represents a quantity of charge provided to a fluid sample held in a test strip 108. Accordingly, this quantity of charge can be used to provide a measurement of the ORP capacity (cORP) of the fluid sample. Moreover, the voltage curves 608 represent a static ORP (sORP) value of a respective fluid sample at different points in time. The area under the current curve 604 (which is above the curve 604, between that curve and a current of zero in FIG. 6) that is used to determine the cORP can have a start point at a first point in time and an end point at a second point in time. As an example, the start point for integration of the current 604 can be selected as a point at which the observed sORP signal or reading has stabilized. For instance, in the example of FIG. 6, the potential difference values have stabilized after about 50 seconds have elapsed. Moreover, in this example no current is being supplied to the sample by the readout device 104 during the first segment of time leading up to the start point at which current is supplied. That start point can also correspond to the time at which the current 604 begins to be applied at an increasing rate. In accordance with embodiments of the present disclosure, where a curve 608 reaches an inflection point, for example the point at which the rate of change in the measured potential difference is at a maximum (i.e., a point of maximum slope), the integration of the current signal 604 is stopped. For example, looking at curve 608*b*, an inflection point can be seen at about 200 seconds, and integration of the current 604 can thus be performed during the period beginning at 50 seconds and ending at 200 seconds. Alternatively, the integration of the current signal 604 can be stopped after some predetermined period of time. As yet another alternative, the integration of the current signal 604 can be stopped at the earlier of the observation of an inflection point or the expiration of a predetermined period of time.

As can be appreciated by one of skill in the art after consideration of the present disclosure, the measurement of the sORP value can be in units of Volts, and the integration of the current signal or value 604 therefore gives a value representing a quantity of charge in Coulombs. cORP values, as a measure of a quantity of charge, is expressed herein as one over the quantity of charge in Coulombs. In particular, by taking the inverse of the observed quantity of charge, a more normal distribution is obtained, facilitating the application of parametric statistics to observed ORP values. As used herein, the terms ORP capacity, inverse capacity levels, inverse capacity ORP or ICL are all equivalent to cORP as defined above. It will be appreciated that expression of cORP as one over a quantity of charge encompasses alternative equivalent expressions.

As noted above, higher than normal values of sORP are indicative of oxidative stress and are considered to be a negative indication for the subject being evaluated. cORP is a measure of a subject's capacity to withstand oxidative insult. Thus, it is a positive indication for a subject to have a normal or higher capacity to withstand oxidative insult. Since cORP is defined as the inverse of the quantity of charge to reach a voltage inflection point, a higher cORP value is indicative of a lesser capacity to withstand oxidative insult, and likewise, a lower cORP value is indicative of a greater capacity to withstand oxidative insult.

The present invention includes embodiments for monitoring or evaluating the health of patients having a variety of conditions by determining the ORP characteristics of a biological sample of the patient. Typically, the ORP characteristics of the patient are compared to an ORP characteristic reference value or values that are relevant to that patient. As used herein, a reference value can be an ORP characteristic of the patient from a time when the patient did not have the condition in question (i.e., when he/she was healthy) or from an earlier time period when the patient had the condition in question (for purposes of monitoring or evaluating the condition or treatment thereof). Such reference values are referred to as self reference values. For example, reference values can also include initial, maximum and ending reference values, such as when ORP characteristics are evaluated over a time frame such as when a patient is being admitted to a medical facility (initial), during a stay at a medical facility (maximum), and at a time when a patient is being considered for transfer, discharge, or other disposition (ending). Alternatively, a reference value can be an ORP characteristic of a relevant healthy population (e.g., a population that is matched in one or more characteristics of species, age, sex, ethnicity, etc.). Such reference values are referred to as normal reference values. Further, a reference value can be an ORP characteristic of a relevant population similarly situated as the patient (e.g., a population having the same or similar condition as the patient for which the patient is being treated and preferably, one that is also matched in one or more characteristics of species, age, sex, ethnicity, etc.). Such a reference value is referred to as a condition specific reference value. For example, a condition specific reference value can be a cancer reference value or a neurodegenerative reference value.

As used herein, a subject is any individual for whom a biological sample is being tested for an ORP characteristic. The term subject can include patient if the subject is an individual being treated by a medical professional. The terms subject and patient can refer to any animal, including humans and non-human animals, such as companion animals (e.g., cats, dogs, horses, etc.) and livestock animals (i.e., animals kept for food purposes such as cows, goats, chickens, etc.). Preferred subjects include mammals and most preferably include humans.

In various embodiments of the invention, the ORP characteristics of a biological sample of a subject are measured. The measurement of the ORP characteristics of a biological sample can done at multiple time points. The frequency of such measurements will depend on the condition being evaluated. For example, urgent conditions such as sepsis can employ more frequent testing of an individual. In contrast, chronic conditions such as neurodegenerative conditions can employ longer term testing intervals. As such, for example, testing can be done every 30 minutes, hour, 2 hours, 3 hours, 4 hours, 5 hours, 6 hours, 12 hours, 18 hours, or day for more urgent conditions. Alternatively, testing can be done every day, 2 days, 3 days, 4 days, 5 days, 6 days, week, 2 weeks, 3 weeks, month, 2 months, 3 months, 4 months, 5 months, 6 months, 7 months, 8 months, 9 months, 10 months, 11 months, or year for more chronic conditions.

In various embodiments of the invention, the ORP characteristics of a biological sample of a subject are measured for purposes of diagnosing, evaluating or monitoring a subject for a specific condition. In such embodiments, the methods can include identifying in the subject a risk factor, such as a lifestyle or genetic risk factor, for the specific condition and/or a symptom of the specific condition.

Readmission

In one embodiment of the invention, a patient is evaluated for ORP characteristics prior to discharge from a medical facility to determine if the patient, who is at the medical facility for a disease or condition, is or is not at risk of early readmission to a medical facility for the disease or condition or complications thereof. Any patient in a medical facility can be evaluated according to the invention. It is particularly important, however, that patients known to be at high risk of early readmission be evaluated prior to discharge. Such patients include patients who (i) required a prolonged period of intensive care or mechanical ventilation, (ii) suffered a stroke, (iii) suffer from cardiovascular diseases (e.g., heart disease, coronary artery disease, myocardial infarction, acute coronary syndrome or heart failure), (iv) have cancer, (v) suffer from pulmonary or respiratory disorders (e.g., pneumonia and other respiratory infections (especially patients who have suffered from complications of pneumonia), chronic obstructive pulmonary disease (COPD), dyspnea, pleural effusion, or hypoxia), (vi) suffer from gastrointestinal disorders, (vii) suffer from sensory disturbances (e.g., pain, fever, vertigo, or sleep apnea), (viii) suffer from renal, urinary or prostate disorders, (ix) suffer from skin disorders or wound infections, (x) suffer from HIV/AIDS, (xi) have diabetes, or (xii) suffer from any other serious illness.

Preferably, a patient is evaluated for a risk of early readmission during the 48 hours, 36 hours, 24 hours and/or 12 hours prior to expected discharge. Early readmission generally refers to readmission within one week, two weeks, three weeks, 30 days, 45 days, 60 days, 75 days or 90 days from the day of discharge.

Medical facilities can include, without limitation hospitals, nursing homes, residential treatment center, skilled nursing facilities, and geriatric care facilities.

This embodiment of the invention includes evaluating a subject who is in a medical facility for treatment of a disease or condition before discharge to determine whether the subject is at risk of readmission to the medical facility for the disease or condition, or complications thereof. A biological sample of the subject is tested for an ORP characteristic which is compared to a readmission reference value to determine the discharge status of the subject. Then a discharge decision for the subject is made based on the discharge status of the subject.

For example, ORP characteristic values of a patient that are significantly elevated compared to the ORP characteristic values of an individual or population that was not readmitted within a relevant time frame indicates that the patient is at risk of early readmission. Similarly, ORP characteristic values of a patient that are not significantly lower compared to the ORP characteristic values of an individual or population that was readmitted within a relevant time frame indicates that the patient is at risk of early readmission. If the patient is at risk for early readmission, the patient's discharge can be postponed or additional treatment after discharge can be prescribed. Such additional treatment after discharge may include referral to extended stay care or early disease management programs at home. These programs can reduce early readmission rates and often include nurse contact within 24 hours after discharge and frequent home check-ups for proper medication compliance and rehabilitation treatments. ORP values that are statistically the same as or lower than that of controls indicates that the patient is not at risk of early readmission.

Diabetes

Another embodiment of this invention provides methods of diagnosing, evaluating or monitoring a subject with diabetes mellitus that includes measuring the ORP characteristics of a biological sample from the subject. The ORP characteristics are compared with the ORP characteristics of a diabetes reference value to evaluate whether they are significantly different and to determine the diabetes status of the subject. The subject is treated based on the diabetes status.

ORP characteristics of the subject may be used to diagnose, evaluate and/or monitor the progress of diabetes in the subject or the development of diabetic complications in the subject or the regulation of blood sugar levels in the subject over time, i.e., the effective compliance of the subject with prescribed diabetic treatments. Such treatments can include insulin administration, oral hypoglycemic agents, exercise, and/or a diabetic diet.

Elevated ORP characteristics of a subject are indicative of rapidly progressing diabetes or diabetic complications in the subject and can indicate a need to change or increase anti-diabetic therapies or implement additional therapies, including but not limited to antioxidant therapy.

In order to determine the trend of ORP characteristics in a diabetic subject over time, without limitation, the ORP characteristics of the subject may be checked every 1, 2, 3, 4, 5, 6, 7, 8, 9, 10, 11 or 12 months after the initial determination of the disease or condition for a period of years or indefinitely, in order to compare and determine a trend in the ORP characteristics of the subject or to assess the status of the subject at a given point in time. If the diabetic subject is admitted to an emergency or hospital care unit, the subject may be monitored at frequent intervals over the entire period of stay prior to discharge and in some embodiments, the change in the ORP characteristics may be at least one factor considered in determining the appropriate discharge date.

The ORP characteristics of the subject may be obtained from a biological sample of the subject, including but not limited to blood, plasma, serum, and cerebrospinal fluid (CSF) in a convenient and timely manner. The ORP of the subject may also be obtained from a tissue of the subject including, but not limited to, pancreatic, ocular or kidney tissue.

Sepsis

Another embodiment of the invention provides methods of diagnosing, evaluating or monitoring sepsis in a subject that includes measuring the ORP characteristics of a biological sample from a subject that has been diagnosed with, or is suspected of having septicemia/bacteremia potentially leading to inflammation, septic shock and multiple organ dysfunction syndrome/failure, and death. The ORP characteristics of the subject are compared with the ORP characteristics of a reference value, such as that of a biological sample from another subject or group of sepsis patients, to determine the sepsis status of the subject. Alternatively or additionally, it may be determined if the ORP of the subject has increased or decreased compared to a prior ORP characteristics measurement obtained from the same subject. The subject is then treated based on the determined sepsis status.

In one embodiment, ORP characteristics of the subject that are statistically similar to or greater than the ORP characteristics of sepsis patient(s) is diagnostic of sepsis in the subject tested. The ORP value(s) may be used to supplement other diagnostic markers of sepsis in the subject such as one or more of white blood cell count, blood cultures, blood pressure, heart rate, temperature, or chest X-ray.

Similarly, an increase in the ORP characteristics of the subject over time is indicative of the progressive development or worsening of severe infection to sepsis and/or septic shock and/or multiple organ failure. Similarly, an increase in the ORP of the subject over time may also indicate a failure of sepsis treatment measures in a subject diagnosed with sepsis, especially the failure of antibiotic and/or anti-oxidant therapy in the sepsis patient. In order to determine the trend of the ORP characteristics in the subject over time, without limitation, the ORP characteristics value of the subject may be checked every 30 minutes, 1 hour, 2 hours, 3 hours, 4 hours, 5 hours or 6 hours after the initial determination in order to compare and determine a trend in the ORP characteristics of the subject.

The ORP of the subject may be obtained from a biological sample of the subject, including but not limited to blood, plasma, and serum, in a convenient and timely manner. The ORP of the subject may also be obtained from a tissue of the subject, including but not limited to, tissues of the skeletal muscles, liver and/or lung.

In related embodiments, the subject may present with signs and symptoms of sepsis or septic shock or may have been previously diagnosed with sepsis and the subject's ORP value(s) may be used to monitor and/or guide a therapy such as antibiotic therapy, fluid resuscitation, vasopressors or anti-oxidant therapy. In these embodiments, the ORP value of the subject may be checked every 30 minutes, 1 hour, 2 hours, 3 hours, 4 hours, 5 hours or 6 hours after the initial determination in order to compare and determine a trend in the ORP value of the patient. An increase in the ORP values of the subject over the time period of the treatment for sepsis is indicative of inadequate or insufficient or inappropriate antibiotic therapy and/or anti-oxidant therapy and may indicate a need to increase the dose and/or the dosing frequency of the antibiotic therapy and/or anti-oxidant therapy or the need to discontinue the current antibiotic therapy and/or anti-oxidant therapy and switch to another antibiotic therapy and/or anti-oxidant therapy. An ORP value of the subject that is decreasing over the time period of the treatment for sepsis is indicative of a successful antibiotic therapy and/or anti-oxidant therapy in the subject.

Stroke

Another embodiment of the invention provides methods of diagnosing, evaluating or monitoring a subject having or suspected of having a stroke that includes measuring ORP characteristics of a biological sample from a subject that is suspected of having a stroke, and then evaluating if the ORP characteristics are significantly different than the ORP characteristics of a reference value such as a biological sample from another subject or group of subjects known to be having a stroke to determine the stroke status of the subject. Alternatively or additionally, it may be determined if the ORP characteristics have increased or decreased compared to a prior ORP characteristics measurement obtained from the same subject. The subject is then treated based on the stroke status.

In one embodiment, the ORP characteristics measurement are taken in addition to other patient diagnostic criteria such as one or more of vital signs, ECG, blood sugar level, CT scan (CAT Scan, Computed axial tomography), MRI (Magnetic resonance imaging, MR), MRA (Magnetic resonance angiogram), Cerebral arteriogram (Cerebral angiogram, Digital subtraction angiography), PT (Prothrombin time) or PTT (Partial thromboplastin time), in order to diagnose stroke and/or rule out such diagnoses as drug overdose, hyper/hypoglycemia, seizure, head trauma, intracranial mass, migraine, meningitis, encephalitis, cardiac and arrest ischemia. Additionally, the ORP characteristics measurement may be used alone or in conjunction with the other diagnostic criteria described above to evaluate the use of fibrinolytic therapy or other acute interventions.

In these emergency care situations, ORP characteristics of the subject that are statistically similar to or greater than the ORP characteristics of a subject or group of subjects diagnosed with stroke is indicative of a stroke in the subject and may indicate use of fibrinolytic therapy in the subject and/or admission to a hospital care unit. Alternatively, ORP characteristics of the subject that are statistically similar to a subject or group of "normal" subjects that are not affected by stroke is indicative of other sources of neurological distress and may suggest no intervention with fibrinolytic therapy in the subject.

An increase in the ORP characteristics of the subject over time following initial presentation of the subject may be indicative of developing brain damage in the stroke patient. In order to determine the trend of the ORP characteristics in the subject over time, without limitation, the ORP characteristics value of the subject may be checked every 1, 2, 3, 4, 5, 6, 7, 8, 9, or 10 minutes after the initial determination for a period of 1, 2, 3, or 4 hours, in order to compare and determine a trend in the ORP characteristics value of the subject. If the subject is admitted to a hospital care unit, the subject may be monitored at frequent intervals over the entire period of stay prior to discharge and in some embodiments, the change in the ORP characteristics values may be at least one factor considered in determining the appropriate discharge date.

The ORP characteristics of the subject may be obtained from a biological sample of the subject, including but not limited to blood, plasma, serum, and cerebrospinal fluid (CSF) in a convenient and timely manner. The ORP characteristics of the subject may also be obtained from a tissue of the subject, including but not limited to, brain tissue biopsy.

Cardiovascular Diseases

Atherosclerosis and its related cardiovascular morbidity and mortality, underlie many chronic diseases. Most atherosclerotic patients have multiple cardiovascular risk factors, which potentiate each other, causing a huge burden on health systems. Oxidative stress has a major role in the pathogenesis of atherosclerosis.

Another embodiment of this invention provides methods of diagnosing, evaluating or monitoring a cardiovascular disease, disorder, or condition in a subject that includes measuring the ORP characteristics of a biological sample from a subject that has been diagnosed with, or is suspected of having or developing a cardiovascular disease, disorder or condition, and then evaluating if the ORP characteristics are significantly different than a reference value such as the ORP characteristics of a biological sample from another subject or group of subjects known to be free of the cardiovascular disease, disorder or condition. Alternatively or additionally, it may be determined if the ORP characteristics have increased or decreased compared to a prior ORP characteristics measurement obtained from the same subject. The subject is then treated based on the cardiovascular disease status. Suitable treatments can include thrombolytic therapy, angioplasty, cardiac catheterization, or treatment of reperfusion injury.

In one embodiment, the cardiovascular disease is a disorder such as heart failure, atherosclerosis, ischemic heart disease, myocardial hypertrophy, hypertension, hypercholesterolemia, hyperlipidemia, sinus node dysfunction and related rhythm abnormalities, especially atrial fibrillation, type 2 diabetes, renal failure with varying degrees of insufficiency; chronic kidney disease (CKD) not on renal replacement therapy (RRT); continuous ambulatory peritoneal dialysis (CAPD) and hemodialysis (HD).

In such disorders, ORP characteristics of the subject that are significantly greater than the ORP characteristics of subjects known to be free of cardiovascular disease and/or atherosclerosis is indicative of the development or worsening of cardiovascular disease and/or atherosclerosis in the subject. Similarly, an increase in the ORP characteristics of the subject over time is indicative of the development or worsening of cardiovascular disease and/or atherosclerosis in the subject. In order to determine the trend of the ORP characteristics in the subject over time, without limitation, the ORP characteristics value of the subject may be checked every 1, 2, 3, 4, 5, or 6 months after the initial determination in order to compare and determine a trend in the ORP characteristics value of the patient.

The ORP characteristics of the subject may be obtained from a biological sample of the subject, including but not limited to blood, plasma, and serum, in a convenient and timely manner. The ORP characteristics of the subject may also be obtained from a tissue of the subject, including but not limited to, tissues of the myocardium (e.g., epicardium, endocardium, base, apex) and/or tissues of the immune system (e.g., peripheral polymorphonuclear leukocytes (PMNLs)).

In a related embodiment, a subject may present with chest pain and the ORP characteristics of the subject are obtained and compared to an ORP characteristics value from subjects undergoing cardiac arrest and/or subjects known to be "normal" or free of cardiovascular disease. An ORP characteristics value of the subject that is statistically similar to, or greater than, the ORP characteristics value from subjects undergoing cardiac arrest is indicative of a patient experiencing or at elevated risk of developing cardiac arrest. In this circumstance, the subject may be admitted to a hospital or care unit, or processed for further evaluation that may include obtaining and evaluating an EKG from the subject and/or enzyme levels associated with cardiac arrest, such as troponin (types cTnI and/or cTnT) creatine kinase, and myoglobin. The ORP characteristics value of the subject may be checked every 30 minutes, 1 hour, 2 hours, 3 hours, 4 hours, 5 hours or 6 hours after the initial determination in order to compare and determine a trend in the ORP characteristics value of the patient.

An ORP characteristics value of the subject that is statistically similar to, or less than, the ORP characteristics value from "normal" subjects is indicative of a patient at no or low risk of cardiac arrest. In this circumstance, the subject may be discharged or otherwise released from any further evaluation. Similarly, the ORP characteristics value of such subject may be checked every 1 to 6 hours after the initial determination in order to compare and determine a trend in the ORP characteristics value of the patient.

Athletics

Another embodiment of the invention provides methods of evaluating or monitoring athletic performance in a subject that includes measuring the ORP characteristics of a biological sample from a subject athlete, and then evaluating if the ORP characteristics are significantly different than the ORP characteristics of a reference value such as biological sample from the subject athlete at an earlier time point during a training program. Alternatively or additionally, the ORP characteristics of the subject may be compared to the ORP characteristics of a target population. The subject athlete is then treated by preparing a training program based on the measured ORP characteristics. For example, such a training program can include a new or modified program, which can include more or less rigorous training requirements than the athlete is currently performing and/or modified nutrition and/or supplementation. The training program can then be executed by the athlete.

The method is suitable for any athlete or individual engaging in athletic endeavors. More particularly the athlete can be an endurance athlete or a strength athlete and can be male or female. The type of athletic endeavor can be resistance exercise, including acute heavy resistance exercise. Such exercise can be weightlifting, sprinting, field events, football, martial arts, wrestling, or boxing. The exercise can also be endurance exercise, such as running, cycling, swimming, hiking, triathalon, softball, baseball, soccer, basketball, hockey, football, rugby, tennis, and lacrosse.

In order to determine the trend of the ORP characteristics in the subject over time, without limitation, the ORP characteristics value of the subject may be checked during a training program, such as every 1, 2, 3, or 4 weeks or every 1, 2, 3, 4, 5, or 6 months to compare and determine a trend in the ORP characteristics value of the athlete.

ORP characteristic testing may be used alone or in conjunction with other athletic/athlete testing and evaluation methodologies, such as $VO_2$ maximum, anaerobic threshold test, Wingate test, critical power, resting metabolic rate, body composition, speed testing, power testing, strength testing, flexibility testing, muscle biopsy, fast twitch fiber test, slow twitch fiber test, and ACTN3 genetic testing.

In certain embodiments, ORP characteristic values and comparison with ORP characteristic values of other athletes may be used to design training regimens that may be optimally designed for the subject.

In certain embodiments, ORP characteristic values and comparison with ORP characteristic values of other athletes may be used to identify risk factors or potential hazards for participation in athletic activities. Such risk factors may include identification of increased chance of injury to the subject.

In certain embodiments, ORP characteristic values and comparison with ORP characteristic values of other athletes may be used to monitor recovery time and progress following a sports injury. In one such embodiment, ORP characteristic values may help to determine the presence of, and/or recovery from, a concussion in the subject. In another such embodiment, ORP characteristic values are obtained during the subject's recovery time and the values are used to determine the fitness and extent of recovery of the athlete to return to the athletic performance.

In certain embodiments, ORP characteristic values and comparison with ORP characteristic values of other athletes may be used to provide prognostic information about the likely performance of a subject in an athletic event or performance. In some embodiments, ORP characteristic value comparisons with ORP characteristic values of other athletes may be indicative of the subject's performance in specific sports events such as power/sprinter athletic events or athletic events requiring endurance.

In certain embodiments, ORP characteristic values and comparison with ORP characteristic values of other athletes may be used to provide information about the performance of a subject during an athletic event to maximize the subject's performance during the event or to minimize risk or harm to the subject during the event.

In certain embodiments, ORP characteristic values and comparison with ORP characteristic values of other athletes may be used to help design workout or practice regimens for athletes based on the ORP characteristic values obtained during or shortly after the participation in the athletic event.

In certain embodiments, ORP characteristic values and comparison with ORP characteristic values of other athletes may be used to provide a feedback or a monitoring mechanism to establish a baseline to measure progress from earlier training periods and/or cycles to subsequent training periods.

Neurodegenerative Disorders

Reactive oxygen species (ROS) and oxidative damage are important factors in the processes involved in neurodegenerative disorders. Reduction of the antioxidant defenses can lead to an increase in the oxidation of critical proteins in neurons in the brain, particularly in Alzheimer's disease.

Another embodiment of the present invention provides methods of diagnosing, evaluating or monitoring a neurodegenerative disease, disorder, or condition in a subject that includes measuring the ORP characteristics of a biological sample from a subject that has been diagnosed with, or is suspected of having or developing a neurodegenerative disease, disorder or condition, and then evaluating if the ORP characteristics are significantly different than the ORP characteristics of a reference value such as a biological sample from another subject or group of subjects known to be free of the neurodegenerative disease, disorder or condition to determine the neurodegenerative disorder status of the subject. Alternatively or additionally, it may be determined if the ORP characteristics from the subject have increased or decreased compared to a prior ORP characteristics measurement obtained from the same subject. The subject is then treated based on the neurodegenerative disorder status.

The neurodegenerative disease may be a disease or disorder such as Parkinson's Disease (PD), Parkinsonian-like syndromes such as Amyotrophic Lateral Sclerosis (ALS) and Progressive Supranuclear Palsy (PSP), Alzheimer's Disease (AD) and poly Q disorders such as Huntington's disease. In such disorders, an elevation in the ORP characteristics of the subject over the ORP characteristics of subjects known to be free of neurological disorder is indicative of the development or worsening of a neurological disorder in the subject. Similarly, an increase in the ORP characteristics of the subject over time is indicative of the development or worsening of neurological disorder in the subject. In order to determine the trend of the ORP characteristics in the subject over time, without limitation, the ORP characteristics value of the subject may be evaluated every 1, 2, 3, 4, 5, 6, 7, 8, 9, 10, 11, or 12 months after the initial determination in order to compare and determine a trend in the ORP characteristics value of the patient.

The ORP characteristics of the subject may be obtained from a biological sample of the subject, including but not limited to blood, plasma, and serum, in a convenient and timely manner. The ORP characteristics of the subject may also be obtained from a tissue of the subject, including but not limited to, tissues of the central nervous system (e.g., cerebrospinal fluid, brain or spinal tissues).

ORP characteristics of a subject that are statistically similar to, or less than, the ORP characteristics value from "normal" subjects is indicative of a patient at no or low risk of developing a neurological disorder. In this circumstance, further evaluation of the subject can be discontinued. Alternatively, an ORP characteristics value of the subject that is statistically similar to, or greater than, the ORP characteristics value from subjects having a neurological disorder, is indicative of a subject at moderate or elevated risk of developing a neurological disorder. Such a subject can be recommended for further evaluation and/or repeated or regular evaluation of ORP characteristics values to evaluate or monitor potential progress in developing a neurological disorder. Such a patient may also be recommended for administration of antioxidant therapy, such as administration of a cocktail of multiple antioxidants, psychological treatment for cognitive disorders and/or anti-inflammatory agents beneficial in the prevention of neurodegenerative disease.

Evaluation of Patients in Critical Care Setting

Critically ill patients suffer from oxidative stress as critical illness can drastically increase the production of reactive oxygen or nitrogen species while these patients have reduced plasma and intracellular levels of antioxidants and free electron scavengers or cofactors, and decreased activity of the enzymatic system involved in detoxification of reactive oxygen or nitrogen species. The pro-oxidant/antioxidant balance is of functional relevance during critical illness because it is involved in the pathogenesis of multiple organ failure. Thus, there is a significant relationship between oxidative stress and severity in critically ill patients.

A further embodiment of the invention provides methods of diagnosing, evaluating or monitoring critically ill patients and the severity of their condition by measuring the ORP characteristics of a biological sample from such a patient and then evaluating if the ORP characteristics are significantly different than the ORP characteristics of a reference value such as a biological sample from a normal population or from a critically ill population to determine the critically ill status of the patient. The patient is then treated based on the critically ill status.

In one embodiment, the ORP characteristics of a subject are obtained upon intensive care unit (ICU) admission and in order to determine the trend of the ORP characteristics in the subject over time, without limitation, the ORP characteristics value of the subject may be checked every 30 minutes, 1 hour, 2 hours, 3 hours, 4 hours, 5 hours or 6 hours or on a daily or weekly basis after the initial determination in order to compare and determine a trend in the ORP characteristics of the subject. These ORP evaluations may be used in conjunction with other markers of oxidative stress/capacity such as monitoring of dietary intake of antioxidant vitamins (A, C and E) Sequential Organ Failure Assessment scores, Acute Physiology and Chronic Health Evaluation (APACHE) II scores, specific biological markers of oxidative stress such as lipid peroxides, carbonyl groups, which represent damage to lipids and proteins, and evaluation of the endogenous antioxidants bilirubin, total proteins and uric acid.

An ORP characteristics value of the subject that is statistically similar to, or less than, the ORP characteristics value from "normal" or non-critically ill subjects is indicative of a critical care patient at no or reduced risk of deterioration in condition and/or organ failure. Such subjects may be discharged from the critical care setting and may be prescribed different or reduced antioxidant and/or other therapies with the expectation of improved health and positive medical outcome.

Alternatively, an ORP characteristics value of the subject that is statistically similar to, or greater than, the ORP characteristics value from critical care subjects or who shows significantly greater or persistent worsening in ORP characteristics values, is indicative of a subject at elevated risk of sustained requirements for critical care therapies, or poor medical prognosis or mortality. Such subject may be recommended for further evaluation and/or repeated or regular evaluation of ORP characteristics values and/or administration of one or more antioxidant therapies. In addition, such subjects can be administered fluid resuscitation or have their vital signs monitored Cancer Oxidative stress, chronic inflammation, and cancer are closely linked. Mechanisms by which oxidative stress leads to chronic inflammation, which in turn can mediate chronic diseases such as cancer include the activation of a variety of transcription factors (including NF-κB, AP-1, p53, HIF-1α, PPAR-γ, β-catenin/Wnt) leading to the expression of growth factors, inflammatory cytokines, chemokines, cell cycle regulatory molecules, and anti-inflammatory molecules, which may lead to the transformation of normal cells, and effect tumor cell survival, proliferation, chemoresistance, radioresistance, invasion, angiogenesis and stem cell survival.

Another embodiment of the invention is a method of diagnosing, evaluating and/or monitoring cancer in a subject by measuring the ORP characteristics of a biological sample from such a subject and then evaluating if the ORP characteristics are significantly different than the ORP characteristics of a reference value such as a biological sample from a normal population or from a cancer population to determine the cancer status of the subject. The subject is then treated based on the cancer status. In various embodiments, the cancer can be any type of cancer, including a solid tumor, a leukemia or lymphoma or a metastatic disease. In such cancer, ORP characteristics of the subject that are significantly greater than the ORP characteristics of subjects known to be cancer free is indicative of the presence or worsening of a cancer in the subject. Similarly, an increase in the ORP characteristics of a cancer patient over time is indicative of the development or worsening of the cancer and potentially the development of metastatic disease. In order to determine the trend of the ORP characteristics in such patient over time, the ORP characteristics value of the subject may be checked every 1 to 6 months after the initial determination in order to compare and determine a trend in the ORP characteristics value of the patient.

The ORP characteristics of the subject may be obtained from a biological sample of the subject, including but not limited to blood, plasma, and serum. The ORP characteristics of the subject may also be obtained from a tissue of the subject, including but not limited to, organ tissues or tumor biopsies.

Thus, in one embodiment, a subject suspected of having a cancer may be evaluated for ORP characteristics values indicative of cancer in the subject or in a specific tissue of the subject. An ORP characteristics value of the subject that is statistically similar to, or less than, the ORP characteristics value from subjects known to be cancer free or "normal" is indicative of a subject that is cancer free or such value may be used to rule out a cancer diagnosis, either alone or in conjunction with other diagnostic procedures. An ORP characteristics value of the subject that is statistically similar to, or greater than, the ORP characteristics value from subjects known to have cancer, and a specific cancer type, or grade is indicative of a subject that has cancer or such value may be used to determine the type of cancer in the subject or the tumor grade. The ORP characteristics values of such subject may be checked regularly after the initial determination in order to re-evaluate the initial cancer diagnosis or to continue or evaluate or monitor tumor grade in a cancer patient.

In a related embodiment, a patient diagnosed with a cancer and undergoing anti-cancer therapy may be regularly monitored by evaluation of ORP characteristics values indicative of successful or unsuccessful anti-cancer therapy. An ORP characteristics value of the subject that is statistically similar to, or less than, the ORP characteristics value from subjects known to be cancer free or successfully responsive to certain cancer therapies is indicative of a patient responding to a cancer therapy and/or having a positive prognosis for cancer survival or remission Likewise, an ORP characteristics value of the subject that is statistically similar to, or less than, the ORP characteristics value from prior ORP characteristics values of the same subject prior to or earlier in treatment is indicative of a patient responding to a cancer therapy and/or having a positive prognosis for cancer survival or remission. In these circumstances, the subject may be continued on the same anti-cancer therapy or even discontinued from therapy. The ORP characteristics values of such subject may be checked, without limitation, every 1, 2, 3, 4, 5, or 6 months after the initial determination in order to evaluate the prolonged survival and monitor reoccurrence of a cancer in the subject or the development of a metastatic disease.

Alternatively, an ORP characteristics value of the subject that is statistically similar to, or greater than, the ORP characteristics value from subjects known to have the same cancer or to have progressed to a higher grade tumor or to have succumbed to cancer, is indicative of a cancer patient that is not responding to a specific cancer therapy and/or having a negative or poor prognosis for cancer survival or remission. In this circumstance, the subject may be discontinued on an anti-cancer therapy or recommended for a change in anti-cancer therapy, such as the addition of an additional anti-cancer therapy or change to a different anti-cancer therapy. Anti-cancer therapies can include without limitation surgery, chemotherapy, and radiation.

Obesity/Metabolic Syndrome

Obesity induces systemic oxidative stress and increased oxidative stress in accumulated fat and has been linked with dysregulation of adipocytokines and development of metabolic syndrome.

Another embodiment of the invention is a method of diagnosing, evaluating and/or monitoring obesity in a subject as well as monitoring progress in a weight loss regimen, which may include diet and/or exercise regimens by measuring the ORP characteristics of a biological sample from such a subject and then evaluating if the ORP characteristics are significantly different than the ORP characteristics of a reference value such as a biological sample from a normal population or from an obese population to determine the obesity and/or metabolic syndrome status of the subject. The subject is then treated based on the obesity and/or metabolic syndrome status of the subject. In these methods, an increase in the ORP characteristics of the subject over the ORP characteristics of subjects of normal or average body mass index (BMI) is indicative of the presence or worsening of the obesity in the subject. Alternatively, or in addition, an increase in the ORP characteristics of the subject over the ORP characteristics of other obese subjects having a similar or greater BMI than the tested subject, is indicative of the presence or worsening of the obesity in the subject.

Similarly, an increase in the ORP characteristics of an obese subject over time is indicative of the progression or worsening of the obesity or metabolic syndrome in the subject. In order to determine the trend of the ORP characteristics in such subjects over time, without limitation, the ORP characteristics value of the subject may be checked every 1, 2, 3, 4, 5, or 6 weeks or every 1, 2, 3, 4, 5, or 6 months after the initial determination in order to compare and determine a trend in the ORP characteristics value of the subject.

The ORP characteristics of the subject may be obtained from a biological sample of the subject, including but not limited to blood, plasma, and serum. The ORP characteristics of the subject may also be obtained from a tissue of the subject, including but not limited to, fat tissue biopsies.

In one embodiment, an obese subject undertaking a weight loss regimen may be evaluated for ORP characteristics values indicative of increasing obesity or progressive weight loss in the subject in a specific tissue of the subject. An ORP characteristics value of the subject that is statistically similar to, or less than, the ORP characteristics value from subjects with normal or low BMI is indicative of a subject that is progressing to weight loss, either alone or in conjunction with other diagnostic procedures. An ORP characteristics value of the subject that is statistically similar to, or greater than, the ORP characteristics value from other obese subjects is indicative of a subject that is not progressing to weight loss or is gaining weight or progressing to the development or worsening of metabolic syndrome. The ORP characteristics values of such subject may be evaluated regularly after the initial determination in order to re-evaluate the initial evaluation of weight loss or disease progression.

In a related embodiment, an obese subject undergoing a weight loss regimen may be regularly monitored by evaluation of the subject's ORP characteristics values compared with ORP characteristics values indicative of successful or unsuccessful weight loss regimen(s). An ORP characteristics value of the subject that is statistically similar to, or less than, the ORP characteristics value from subjects having a normal or lower BMI compared with the subject, or ORP characteristics values of subjects successfully reducing weight in a weight loss regimen is indicative of a subject successfully losing weight and/or having a positive prognosis for losing or maintaining weight or overcoming metabolic syndrome. In this circumstance, the subject may be continued on the same anti-obesity regimen or even discontinued from a regimen. Without limitation, the ORP characteristics values of such subject may be checked every 1, 2, 3, 4, 5, or 6 weeks every 1, 2, 3, 4, 5, or 6 months after the initial determination in order to evaluate the subject's progress and/or disease prognosis.

Alternatively, an ORP characteristics value of the subject that is statistically similar to, or greater than, the ORP characteristics value from obese subjects having the same or greater BMI as the subject tested is indicative of a subject that is not responding to a specific weight loss regimen and/or having a negative or poor prognosis for developing or worsening metabolic syndrome. In this circumstance, the subject may be discontinued on the weight loss regimen or recommended for a change in the weight loss regimen, such as the addition of additional weight-loss therapies or change to a different weight loss regimen.

Hemodialysis

Dialysis is associated with an increased generation of oxidants, which play an important part in the development of atherogenesis and inflammation.

One embodiment of the invention is a method of monitoring hemodialysis in a subject as well as monitoring the need for iron replacement therapy in a dialysis patient by measuring the ORP characteristics of a biological sample from such a subject and then evaluating if the ORP characteristics are significantly different than the ORP characteristics of a reference value such as a biological sample from a normal population or from a dialysis population to determine the hemodialysis status of the subject. The subject is then treated based on the hemodialysis status of the subject. In these methods, an increase in the ORP characteristics of the patient over the ORP characteristics of patients of normal kidney function is indicative of the need for reduction in the frequency of dialysis or reduced iron replacement therapy.

In order to determine the trend of the ORP characteristics in the subject over time, without limitation, the ORP characteristics value of the subject may be checked after every hemodialysis treatment in order to compare and determine a trend in the ORP characteristics of the subject.

Brain Injury

Brain tissue is particularly vulnerable to oxidative damage because of its high rate of metabolic activity, accompanied by intensive production of reactive oxygen metabolites, relatively low antioxidant capacity, low repair mechanism activities, the non-replicating nature of neuronal cells, and the high membrane surface-to-cytoplasm ratio. The high concentrations of polyunsaturated fatty acids in the membrane lipids of the brain are the source for lipid peroxidation in which initiating free radicals can precipitate destruction of adjacent lipid molecules. The brain also contains high levels of transition metals, such as iron, which are located in specific sites in the brain (e.g., substantia nigra) and are capable of catalyzing the production of highly toxic radicals via the metal-mediated Haber-Weiss reaction.

The physiological response to brain injury is extremely complex and involves the activation of an overlapping network of humoral, tissue, and cellular pathways. The initiating injury triggers the release of endogenous mediators, which initiate a cascade of molecular, cellular, and tissue responses resulting in delayed tissue edema, necrosis, and impaired function. It has been suggested that the initial events in blunt head trauma lead to a final common pathway of neuronal death involving loss of cellular calcium homeostasis, production of free radicals, and tissue acidosis (Siesjo B K, Agardh C D & Begtsson F. (1989) Free radicals and brain damage. Cerbrovasc Brain Metab Rev 1: 165-211). A number of therapeutic approaches, based on intervention by scavenging ROS, have been attempted both in experimental models and in the clinical setting, but a practical and effective method of identifying and/or monitoring the oxidative status of a patient that has suffered a brain injury or is suspected of sustaining a brain injury is needed.

Another embodiment of the invention provides methods of diagnosing, evaluating or monitoring a brain injury in a subject that includes measuring the ORP characteristics of a biological sample from a subject that has been diagnosed with, or is suspected of having or developing a brain injury, and then evaluating if the ORP characteristics are significantly different than the ORP characteristics of a reference value such as the same biological sample from another subject or group of subjects having no brain injury, disorder or condition to determine the brain injury status of the subject. The subject is then treated based on the brain injury status of the subject. Alternatively or additionally, it may be determined if the ORP characteristics have increased or decreased compared to a prior ORP characteristics measurement obtained from the same subject. In a specific embodiment, this may include comparison to an ORP characteristics measurement obtained from the same subject taken before the suspected or confirmed brain injury occurred.

In one embodiment, the brain injury is a traumatic brain injury causing damage to the brain resulting from events such as external mechanical force, rapid head acceleration or deceleration, impact, blast waves, or penetration of the head by a projectile.

In such injuries, an increase in the ORP characteristics of the subject over the ORP characteristics of subjects known to be free of brain injury is indicative of the development or worsening of the injury or subsequent functional impairments in the subject. Similarly, an increase in the ORP characteristics of the subject over time is indicative of the development or worsening of brain injury in the subject. In order to determine the trend of the ORP characteristics in the subject over time, without limitation, the ORP characteristics value of the subject may be checked every 1, 2, 3, 4, 5, or 6 days or weeks after the initial determination in order to compare and determine a trend in the ORP characteristics value of the patient.

The ORP characteristics of the subject may be obtained from a body fluid of the subject, including but not limited to blood, plasma, cerebrospinal fluid (CSF) and serum, in a convenient and timely manner. The ORP characteristics of the subject may also be obtained from a tissue of the subject, including but not limited to, tissues of the brain.

In a related embodiment, the subject may present with symptoms of head injury, such as dizziness, nausea, vomiting, loss of consciousness, headache, vomiting, nausea, lack of motor coordination, difficulty balancing, lightheadedness, blurred vision, tinnitus, fatigue or lethargy, changes in sleep patterns, behavioral or mood changes, confusion, trouble with memory, concentration, or attention, and the ORP characteristics of the subject are obtained and compared to an ORP characteristics value from one or more subjects known to have undergone head injury and/or subjects known to be "normal" or free of head injury. An ORP characteristics value of the subject that is statistically similar to, or greater than, the ORP characteristics value from subjects known to have sustained head injury is indicative of a patient experiencing or at elevated risk of developing permanent neural injury or functional deficits. In this circumstance, the subject may be admitted to a hospital or care unit, or processed for further evaluation that may include obtaining and evaluating brain scans. Possible treatments for brain injury include medication (e.g., pain relievers, diuretics, anti-seizure drugs or coma-inducing drugs), surgery (e.g., removing clotted blood, repairing skull fractures, or opening a window in the skull), rehabilitation (e.g., physiatry, occupational therapy, physical therapy, speech and language pathology, or neuropsychology). The ORP characteristics value of the subject may be checked every 1 to 6 hours after the initial determination in order to compare and determine a trend in the ORP characteristics value of the subject.

An ORP characteristics value of the subject that is statistically similar to, or less than, the ORP characteristics value from "normal" subjects is indicative of a subject lacking a brain injury at no or low risk of further brain damage. In this circumstance, the subject may be discharged or otherwise released from any further evaluation. Similarly, the ORP characteristics value of such subject may be checked every 1 to 6 hours after the initial determination in order to compare and determine a trend in the ORP characteristics value of the patient.

Pregnancy/Fetal Health

Pregnancy is a prolonged state of oxidative stress arising from increased placental mitochondrial activity and production of reactive oxygen species. Excessive production of ROS may occur at certain windows in placental development and in pathologic pregnancies, such as those complicated by preeclampsia and/or IUGR, overpowering antioxidant defenses, with deleterious outcome. For example, in the first trimester, establishment of blood flow into the intervillous space is associated with a burst of oxidative stress. The inability to mount an effective antioxidant defense against this may result in early pregnancy loss. Oxidative stress peaks by the second trimester of pregnancy, ending what appears to be a vulnerable period for fetal health and gestational progress. In late gestation, increased oxidative stress may be seen in pregnancies complicated by diabetes, IUGR, and preeclampsia.

Another embodiment of this invention is a method of diagnosing, evaluating and/or monitoring pregnancy in a subject as well as monitoring progress in fetal development or risk by measuring the ORP characteristics of a biological sample from such a subject and then evaluating if the ORP characteristics are significantly different than the ORP characteristics of a reference value, such as a biological sample from a non-pregnant population or from a pregnant population to determine the pregnancy and/or fetal development status of the subject. The subject is then treated based on the pregnancy and/or fetal development status. In these methods, an increase in the ORP characteristics of the subject over the ORP characteristics of non-pregnant subjects is indicative of the presence of pregnancy in the subject. Alternatively, or in addition, an increase in the ORP characteristics of the subject over the ORP characteristics of a reference value from pregnant subjects known to have normal pregnancy of the same gestational period, is indicative of a potential developing maternal or fetal risk or high-risk pregnancy in the subject.

In order to determine the trend of the ORP characteristics in such subjects over time, without limitation, the ORP characteristics value of the subject may be checked every 1, 2, 3, 4, 5, or 6 days or weeks after the initial determination in order to compare and determine a trend in the ORP characteristics value of the subject.

The ORP characteristics of the subject may be obtained from a body fluid of the subject, including but not limited to blood, plasma, amniotic fluids, and serum. The ORP characteristics of the subject may also be obtained from a tissue of the subject, including but not limited to, placental or fetal tissues.

Thus, in one embodiment, a pregnant subject may be evaluated for ORP characteristics values indicative of abnormal pregnancy or increased fetal risk in the subject. An ORP characteristics value of the subject that is statistically similar to, or less than, the ORP characteristics value from subjects known to have a normal pregnancy of the same gestational period is indicative of a subject that is progressing with normal pregnancy. An ORP characteristics value of the subject that is statistically similar to, or greater than, the ORP characteristics value from subjects known to have a normal pregnancy of the same gestational period is indicative of a subject that is not progressing to normal pregnancy or may be progressing to abnormal pregnancy, including preeclampsia or eclampsia, gestational diabetes, or may be at elevated risk of miscarriage or fetal death.

The ORP characteristics values of such subject may be checked regularly after the initial determination in order to re-evaluate the initial evaluation of normal pregnancy or abnormal pregnancy or fetal development or developmental progression. In a related embodiment, a pregnant subject may be regularly monitored by evaluation of the subject's ORP characteristics values compared with ORP characteristics values indicative of normal fetal development. An ORP characteristics value of the subject that is progressing statistically to an ORP characteristics value that is similar to, or greater than, the ORP characteristics value from subjects having a normal pregnancy compared with the subject, is indicative of a subject that may be progressing to unhealthy or abnormal pregnancy.

The ORP characteristics values of such subject may be checked, without limitation, every 1, 2, 3, 4, 5, or 6 weeks or every 1, 2, 3, 4, 5, or 6 months after the initial determination in order to evaluate the subject's pregnancy progress and/or disease prognosis.

In some embodiments, subjects found to have elevated ORP characteristics indicative of abnormal or high-risk pregnancy are administered an antioxidant regimen and/or a regimen of avoidance of iron excess to ameliorate maternal and early fetal damage.

Respiratory Distress

Respiratory distress, including acute respiratory distress syndrome (ARDS), is a lung condition that leads to low oxygen levels in the blood that can be life threatening. Respiratory distress is typically experienced in subjects with a respiratory disorder, such as pneumonia, sepsis, severe bleeding caused by injury, chest or head injury, breathing harmful fumes, or inhaling vomited stomach contents.

Another embodiment of this invention is a method of diagnosing, evaluating and/or monitoring respiratory distress in a subject by measuring the ORP characteristics of a biological sample from such a subject and then evaluating if the ORP characteristics are significantly different than the ORP characteristics of a reference value, such as a biological sample from a population at risk for respiratory distress or from a patient having a respiratory disorder to determine the respiratory distress status of the subject. The subject is then treated based on the respiratory distress status. In these methods, an increase in the ORP characteristics of the subject compared to the ORP characteristics of a healthy or normal subject is indicative of the presence of respiratory distress in the subject. Alternatively, or in addition, progressively increasing ORP characteristics in a subject with a respiratory disorder may be indicative of developing acute respiratory distress syndrome in the subject. Alternatively, the ORP characteristics of the subject may be compared to the ORP characteristics of a healthy or normal subject to rule out respiratory distress in subject experiencing low blood pressure, confusion, and extreme tiredness or other symptoms of respiratory distress.

Subjects who develop respiratory distress often are hospitalized for other health problems. Thus, one embodiment is monitoring the ORP characteristics of a hospitalized patient to identify developing respiratory distress before an acute respiratory distress syndrome is experienced.

In certain embodiments, a subject having an ORP characteristics value indicative of respiratory distress may be administered oxygen therapy, steroids or mechanical ventilation.

In order to determine the trend of the ORP characteristics in such subjects over time, without limitation, the ORP value of the subject may be checked every 1, 2, 3, 4, 5, or 6 minutes, hours or days after the initial determination in order to compare and determine a trend in the ORP characteristics value of the subject.

The ORP characteristics of the subject may be obtained from a body fluid of the subject, including but not limited to blood, plasma, saliva, mucus, respiratory aspirates or other lung fluids, breath condensates, and serum. The ORP characteristics of the subject may also be obtained from a tissue of the subject, including but not limited to, lung tissues.

Childhood Health

Reactive oxygen species (ROS) play a crucial role in the initiation and progression of various diseases in children and adolescents and therefore, the evaluation of oxidative stress in pediatric diseases is an important concern.

Another embodiment of this invention is a method of diagnosing, evaluating and/or monitoring newborn or adolescent health in a child as well as monitoring progress in fetal development or risk by measuring the ORP characteristics of a biological sample from a child and then evaluating if the ORP characteristics are significantly different than the ORP characteristics of a reference value, such as a biological sample from a healthy child or from a child having a known disease state, to determine the childhood health status of the subject. The subject is then treated based on the childhood health status. Such treatment can include identification of a specific disease of the child. In these methods, an increase in the ORP characteristics of the child over the ORP characteristics value of healthy children is indicative of the presence of a disease state or developing disease state in the child. Alternatively, or in addition, an ORP characteristics value of the child similar to the ORP characteristics of a reference value from a healthy child of similar age, may be used to rule out a present or developing disease state in the child. Such developing disease states may include cancer, diabetes and respiratory diseases.

In order to determine the trend of the ORP characteristics in a child over time, without limitation, the ORP characteristics value of the child may be checked every 1, 2, 3, 4, 5, or 6 days or weeks after the initial determination in order to compare and determine a trend in the ORP characteristics value of the child.

The ORP characteristics of the child may be obtained from a body fluid of the subject, including but not limited to blood, plasma, serum, saliva, tears, mucus, pulmonary fluids and urine. The ORP characteristics of the child may also be obtained from a tissue of the child, including but not limited to, skin or hair.

Frailty

Frailty has been thought of as a global measure of one's susceptibility to disease and death; it can also be thought of one's vulnerability to stressors. While varied, frailty has been measured using a combination of the following factors: physical ability, self-reported health, co-morbidities, physiology and psychology. These commonly measured factors have been shown to be associated with a high risk of death and hospitalization, as well as a high use of health care. One of the main limitations of assessing frailty is the lack of a quick, easy-to-use, point-of-care method. Although there are measures of frailty that can be considered quick and easy to administer, they are not as strongly associated with poor outcomes, or rely on a more subjective assessment as compared to the Clinical Frailty Scale of the Canadian Study of Health and Aging (CSHA) or the Fried scale (Frailty in Older Adults: Evidence for a Phenotype. *J Gerontol A Biol Sci Med Sci,* 56(3), M146-157 (2001)).

Another embodiment of this invention provides methods of diagnosing, evaluating or monitoring a subject for frailty that includes measuring the ORP characteristics of a biological sample from a subject that has been diagnosed with, or is suspected of having or developing frailty, and then evaluating if the ORP characteristics are significantly different than a reference value such as the ORP characteristics of a biological sample from another subject or group of subjects known to be frail or known to be fit to determine the frailty status of the subject. The subject is then treated based on the frailty status. Alternatively or additionally, it may be determined if the ORP characteristics have increased or decreased compared to a prior ORP characteristics measurement obtained from the same subject. The ORP characteristics of the subject may be obtained from a biological sample of the subject, including but not limited to blood, plasma, and serum, in a convenient and timely manner.

In such conditions, ORP characteristics of the subject that are significantly greater than the ORP characteristics of subjects known to be fit is indicative of the presence, development or worsening of frailty in the subject. Similarly, an increase in the ORP characteristics of the subject over time is indicative of the development or worsening of frailty in the subject. In order to determine the trend of the ORP characteristics in the subject over time, without limitation, the ORP characteristics value of the subject may be checked every 1, 2, 3, 4, 5, or 6 weeks or months after the initial determination in order to compare and determine a trend in the ORP characteristics value of the patient. Patients who are frail can be treated by maintaining or increasing food intake, resistance exercise, balance exercise, reducing social isolation and controlling geriatric health issues (e.g., depression, impaired vision and hearing, and decreased mobility).

An ORP characteristics value of the subject that is statistically similar to, or less than, the ORP characteristics value from fit subjects is indicative of a patient at no or low risk of frailty. In this circumstance, the subject may be released from any further evaluation.

Determination of ORP characteristics values for subjects at differing levels of frailty can be achieved by evaluating the ORP values for subjects at different grades on the CHSA Clinical Frailty Scale from Grade 1 (Very Fit) to Grade 7 (Severely Frail) or on the Fried scale of Grade 0 (robust), Grade 1 or 2 (intermediate or pre-frail), or Grade 3, 4 or 5 (frail).

Allergy

There is ample evidence that allergic disorders, such as asthma, rhinitis, and atopic dermatitis, are mediated by oxidative stress. Asthma affects 5% to 10% of the population and in asthmatics, oxidative stress occurs not only as a result of inflammation but also from environmental exposure to air pollution. Excessive exposure to reactive oxygen and nitrogen species is the hallmark of oxidative stress and leads to damage of proteins, lipids, and DNA.

Another embodiment of this invention provides methods of diagnosing, evaluating or monitoring an allergic disorder in a subject that includes measuring the ORP characteristics of a biological sample from a subject that has been diagnosed with, or is suspected of having an allergic disorder, and then evaluating if the ORP characteristics are significantly different than a reference value, such as the ORP characteristics of a biological sample from another subject or group of subjects known to be free of allergic disorders, to determine the allergic disorder status of the subject. Alternatively or additionally, it may be determined if the ORP characteristics have increased or decreased compared to a prior ORP characteristics measurement obtained from the same subject. The subject is then treated based on the allergic disorder status.

In such allergic disorders, ORP characteristics of the subject that are significantly greater than the ORP characteristics of subjects without an allergic disorder is indicative of allergic reaction or progressing allergic disorder in the subject. Similarly, an increase in the ORP characteristics of the subject over time is indicative of the progression of the allergic disorder in the subject and may also indicate a failure of a treatment for the allergic disorder.

In order to determine the trend of the ORP characteristics in the subject over time, without limitation, the ORP characteristics value of the subject may be checked every 1, 2, 3, 4, 5, or 6 days, weeks or months after the initial determination in order to compare and determine a trend in the ORP characteristics value of the patient.

The ORP characteristics of the subject may be obtained from a biological sample of the subject, including but not limited to blood, plasma, saliva, mucus and serum, in a convenient and timely manner. The ORP characteristics of the subject may also be obtained from a tissue of the subject, including lung tissues.

In a related embodiment, a subject may present with symptoms of allergic reaction and the ORP characteristics of the subject are obtained and compared to an ORP characteristics value from subjects having an allergic disorder and/or subjects known to be free of allergic disorders. An ORP characteristics value of the subject that is statistically similar to, or greater than, the ORP characteristics value from subjects having an allergic disorder is indicative of a patient having an acute allergic reaction or progression or escalation of an allergic disorder in the subject. In this circumstance, the subject may be treated for an allergic disorder. For example, the subject can be treated by administration of antihistamines, decongestants, steroids, bronchodilators, anti-leukotrienes, or antibody-based therapy or immunotherapy. The ORP characteristics value of the subject may be checked, without limitation, every 1, 2, 3, 4, 5, or 6 hours, days or weeks after the initial treatment in order to compare and determine a trend in the ORP characteristics value of the patient that may be indicative of effective treatment or progression of the allergic reaction. In these instances, the subject may be treated for allergic reaction or disorder. Additionally, therapeutic interventions that decrease exposure to environmental reactive oxygen species or augment endogenous antioxidant defenses might be beneficial as adjunctive therapies for allergic respiratory disorders.

An ORP characteristics value of the subject that is statistically similar to, or less than, the ORP characteristics value from subjects known to be free of an allergic disorder is indicative of a patient that is not experiencing an allergic reaction or having a progressive allergic disorder. In this circumstance, the subject may be released from any further evaluation without treatment for allergic reaction or disorder, or the ORP characteristics value may be used to rule out allergy in the patient. Similarly, the ORP characteristics value of such subject may be checked, without limitation, every 1, 2, 3, 4, 5, or 6 hours or days after the initial determination in order to compare and determine a trend in the ORP characteristics value of the patient, which may reveal the presence of an allergic disorder or the confirmation that the subject is not experiencing an allergic reaction.

Banked Blood Products

After it is donated, human blood begins to lose the ability to facilitate the transfer of oxygen from red blood cells to tissues. Studies have demonstrated that recipients who receive blood transfusions have higher incidences of lung infection, heart attack, heart failure, stroke and even death. It has been shown that banked blood is not the same as blood in the body, as it lacks nitric oxide in red blood cells that opens up blood vessels to facilitate the transfer of oxygen from red blood cells to tissues. It has also been shown that adding this gas back to stored blood products before transfusion appears to restore red blood cells' ability to transfer oxygen to tissues.

Another embodiment of this invention is a method of assessing and/or monitoring the quality of a banked blood product by measuring the ORP characteristics of the banked blood product and then evaluating if the ORP characteristics are significantly different than the ORP characteristics of a reference value, such as a blood sample from a healthy child or adult or from a similar banked blood product known to retain the ability to transfer oxygen to tissues to determine the status of the banked blood product. The banked blood product is then administered to a recipient in need of such treatment or discarded. If the banked blood product is administered, it may be administered in conjunction with a reducing agent (e.g., vitamin C). If administered in conjunction with a reducing agent, the banked blood product may be admixed with a reducing agent prior to administration to the recipient. Alternatively or additionally, the banked blood product may be administered concurrently but separately with a reducing agent to the recipient. If admixed with or administered concurrently with a reducing agent, the ORP characteristics of the banked blood product may be evaluated to determine the amount of a reducing agent to be mixed with the banked blood product or administered to the recipient of the banked blood product.

The ORP characteristics of the banked blood product may be assessed at the time of collecting the banked blood product from a donor or any time thereafter, up to the time of administering the banked blood product to a recipient or discarding the banked blood product. The ORP characteristics of the banked blood product may also be continually assessed for a time period during the storage of the product, including a period extending throughout the entire period of storage of the product.

Anesthesia

Anesthetics may cause oxidative and metabolic stress during administration of anesthesia, such as during surgery, especially coronary surgery, and extracorporeal circulation, leading to organ damage and poor outcome. One embodiment of the invention provides methods of evaluating or monitoring a subject's oxidative stress during administration of anesthesia by assessing the ORP characteristics of a biological sample from the subject and then evaluating if the ORP characteristics are significantly different than the ORP characteristics of a reference value such as the same biological sample from another subject or group of subjects having undergone the same or similar procedure to determine the anesthesia status of the subject. The subject is then treated based on the anesthesia status of the subject. Alternatively or additionally, it may be determined if the ORP characteristics have increased or decreased compared to a prior ORP characteristics measurement obtained from the same subject. In a specific embodiment, this may include comparison to an ORP characteristics measurement obtained from the same subject taken before onset of the administration of anesthesia.

The ORP characteristics value of the subject may be obtained from a body fluid of the subject, including but not limited to blood, plasma, serum, saliva, lung fluids, and breath condensates. The ORP characteristics of the subject may also be obtained from a tissue of the subject, including but not limited to, a tissue of the lung or other organ of the subject.

In order to determine the trend of the ORP characteristics in such subjects over time, without limitation, the ORP value of the subject may be checked every 1, 2, 3, 4, 5, or 6 minutes after the initial determination in order to compare and determine a trend in the ORP characteristics value of the subject.

An ORP characteristics value of the subject that is statistically similar to, or less than, the ORP characteristics value from normal subjects (i.e., not receiving anesthesia) is indicative of a subject that is stable undergoing administration of anesthesia and not in need of emergency measures or adjustment of anesthetic administration during the procedure.

Alternatively, an ORP characteristics value of the subject that is statistically similar to, or greater than, the ORP characteristics value from normal subjects or who shows significantly greater or persistent worsening in ORP characteristics values during administration of anesthesia, is indicative of a subject at elevated risk of oxidative stress, organ damage and poor outcome. Such subject may be treated by adjustment (e.g., titration) to the anesthesia administration or the administration of one or more antioxidant therapies.

Infection

Oxidative stress, primarily due to increased generation of reactive oxygen species (ROS) and reactive nitrogen species (RNS), is a feature of many viral and bacterial infections. ROS and RNS modulate the permissiveness of cells to viral replication, regulate host inflammatory and immune responses, and cause oxidative damage to host tissues.

Another embodiment of this invention provides methods of diagnosing, evaluating or monitoring an infection in a subject that includes measuring the ORP characteristics of a biological sample from a subject that has been diagnosed with, or is suspected of having an infection, and then evaluating if the ORP characteristics are significantly different than a reference value such as the ORP characteristics of a biological sample from another subject or group of subjects known to be free of infection to determine the infection status of the subject. Alternatively or additionally, it may be determined if the ORP characteristics have increased or decreased compared to a prior ORP characteristics measurement obtained from the same subject. The subject is then treated based on the infection status.

In one embodiment, the infection is a viral infection, including RNA viruses, such as influenza viruses, DNA viruses, such as hepatitis B virus, and retroviruses, such as human immunodeficiency virus (HIV).

In another embodiment, the infection is a bacterial infection. Some bacterial infections give rise to oxidative stress in the host when inflammatory cells that express inducible nitric oxide synthase are triggered in an inflammatory process thereby exaggerating the oxidative stress encountered following the bacterial infection.

In such infections, ORP characteristics of the subject that are significantly greater than the ORP characteristics of subjects known to be free of infection are indicative of infection or progressing infection in the subject. Similarly, an increase in the ORP characteristics of the subject over time is indicative of the progression of the infection in the subject and may also indicate a failure of an anti-infective treatment applied to the subject. In order to determine the trend of the ORP characteristics in the subject over time, without limitation, the ORP characteristics value of the subject may be checked every 1, 2, 3, 4, 5, or 6 days or months after the initial determination in order to compare and determine a trend in the ORP characteristics value of the patient.

The ORP characteristics of the subject may be obtained from a biological sample of the subject, including but not limited to blood, plasma, saliva, mucus and serum, in a convenient and timely manner. The ORP characteristics of the subject may also be obtained from a tissue of the subject, including, an infected tissue or organ.

In a related embodiment, a subject may present with symptoms of infection and the ORP characteristics of the subject are obtained and compared to an ORP characteristics value from subjects having an infection and/or subjects known to be free of the infection. An ORP characteristics value of the subject that is statistically similar to, or greater than, the ORP characteristics value from subjects having an infection is indicative of a patient having an infection or progression of an infection in the subject. In this circumstance, the subject may be treated for an infection, for example by the administration of antibiotics, anti-fungal medication or anti-viral medication. The ORP characteristics value of the subject may be checked every 1, 2, 3, 4, 5, or 6 hours or days after the initial treatment in order to compare and determine a trend in the ORP characteristics value of the patient that may be indicative of effective treatment or progression of the infection.

An ORP characteristics value of the subject that is statistically similar to, or less than, the ORP characteristics value from subjects known to be free of an infection is indicative of a patient that is not infected. In this circumstance, the subject may be released from any further evaluation without an anti-infective treatment, or the ORP characteristics value may be used to rule out infection in the patient. Similarly, the ORP characteristics value of such subject may be checked, without limitation, every 1, 2, 3, 4, 5, or 6 hours or days after the initial determination in order to compare and determine a trend in the ORP characteristics value of the patient, which may reveal the presence of an infection or the confirmation that the subject is free of infection.

Trauma

Trauma encompasses a physiological wound caused by an external source. Unintentional and intentional traumatic injuries were the fifth and seventh leading causes of worldwide mortalities, in the 2002 World Health Organization estimates of causes of death by rate. Excessive production of reactive oxygen species due to excitotoxicity and exhaustion of the endogenous antioxidant system may follow traumatic injury in a subject. This oxidative stress in turn induces peroxidation of cellular and vascular structures, protein oxidation, cleavage of DNA, and inhibition of the mitochondrial electron transport chain.

Another embodiment of the invention provides methods of diagnosing, evaluating or monitoring a traumatic injury in a subject that includes measuring the ORP characteristics of a biological sample from a subject that has or is suspected of having experienced a traumatic injury, and then evaluating if the ORP characteristics are significantly different than the ORP characteristics of a reference value such as the same biological sample from another subject or group of subjects that have not experienced a traumatic injury to determine the brain injury status of the subject to determine the trauma status of the patient. The subject is then treated based on the trauma status of the subject. Alternatively or additionally, it may be determined if the ORP characteristics have increased or decreased compared to a prior ORP characteristics measurement obtained from the same subject. In a specific embodiment, this may include comparison to an ORP characteristics measurement obtained from the same subject taken before the suspected or confirmed traumatic injury occurred.

The trauma may include, for example, blunt trauma, traumatic asphyxia, penetrating trauma, chest trauma, abdominal trauma, facial trauma, geriatric trauma, pediatric trauma, polytrauma, blast injury, head injury, spinal cord injury, psychological trauma, and orthopedic trauma, such as bone break or fracture.

In such injuries, an increase in the ORP characteristics of the subject over the ORP characteristics of subjects known to be free of traumatic injury is indicative of the development or worsening of the injury or poor prognosis of the subject. Similarly, an increase in the ORP characteristics of the subject over time is indicative of the development or worsening of injury in the subject. In order to determine the trend of the ORP characteristics in the subject over time, the ORP characteristics value of the subject may be checked every 1 to 6 minutes or days after the initial determination in order to compare and determine a trend in the ORP characteristics value of the patient.

The ORP characteristics of the subject may be obtained from a body fluid of the subject, including but not limited to blood, plasma, cerebrospinal fluid (CSF) and serum, in a convenient and timely manner. The ORP characteristics of the subject may also be obtained from a tissue of the subject, including but not limited to, skin, muscle or bone tissues or tissue from an injured organ. Similarly, the ORP characteristics value of such subject may be checked, without limitation, every 1, 2, 3, 4, 5, or 6 hours after the initial determination in order to compare and determine a trend in the ORP characteristics value of the patient.

The ORP characteristics of the subject are obtained and compared to an ORP characteristics value from one or more subjects known to have undergone similar trauma and/or subjects known to be normal or lacking a traumatic injury. An ORP characteristics value of the subject that is statistically similar to, or greater than, the ORP characteristics value from subjects known to have sustained a traumatic injury is indicative of a patient experiencing or at elevated risk of developing further injury or death or poor prognosis for recovery from traumatic injury. In this circumstance, the subject may be admitted to a hospital or emergency care unit, administered fluid resuscitation, or vasopressors.

An ORP characteristics value of the subject that is statistically similar to, or less than, the ORP characteristics value from "normal" subjects is indicative of a subject that is recovering from a traumatic injury or has a good prognosis for recovery from the traumatic injury and is at lowered risk of death following the traumatic injury. In this circumstance, the subject may be discharged or treated for the injury and discharged without further evaluation.

A related embodiment is a method of predicting or prognosing traumatic orthopedic injury in a subject, including stratification of patients following injury, such as hip fracture in an elderly patient, that includes measuring the ORP characteristics of a biological sample from a subject that is at risk of a traumatic injury, and then evaluating if the ORP characteristics are significantly different than the ORP characteristics of a reference value such as the same biological sample from another subject or group of subjects that are not considered to be at risk of experiencing a traumatic injury to determine the trauma injury risk status of the subject.

An ORP characteristics value of the subject that is statistically similar to, or greater than, the ORP characteristics value from a subject known to have sustained a traumatic orthopedic injury is indicative of a patient at elevated risk of sustaining a traumatic orthopedic injury or is at risk of poor prognosis for recovery from traumatic orthopedic injury. In this circumstance, the subject may be administered antioxidant therapy, or admitted to a medical facility or long term care facility, or provided measures to reduce the risk of experiencing a traumatic orthopedic injury or associated comorbidities.

An ORP characteristics value of the subject that is statistically similar to, or less than, the ORP characteristics value from normal subjects not considered to be at risk of a traumatic orthopedic injury is indicative of a subject that is at low risk of experiencing a traumatic orthopedic injury or has a good prognosis for recovery from a traumatic orthopedic injury and is at lowered risk of death following a traumatic orthopedic injury. In this circumstance, the subject may be discharged from a medical facility or removed from further observation.

Pyloric Stenosis

Pyloric stenosis is a narrowing of the opening from the stomach to the duodenum due to enlargement of the muscle surrounding the pylorus, leading to projectile non-bilious vomiting. It most often occurs in the first few months of life, when it is referred to as infantile hypertrophic pyloric stenosis.

Another embodiment of the invention provides methods of diagnosing, evaluating or monitoring pyloric stenosis in a subject, especially a child subject, that includes measuring the ORP characteristics of a biological sample from the subject that has been diagnosed with, or is suspected of having or developing pyloric stenosis, and then evaluating if the ORP characteristics are significantly different than a reference value, such as the ORP characteristics of a biological sample from another subject or group of subjects known to have pyloric stenosis to determine the pyloric stenosis status of the subject. Alternatively or additionally, it may be determined if the ORP characteristics have increased or decreased compared to a prior ORP characteristics measurement obtained from the same subject. The subject is then treated based on the pyloric stenosis status or diagnosis. Treatment may include the administration of intravenous and/or oral atropine to the subject, or surgery (pyloromyotomy).

Following such diagnosis, ORP characteristics of the subject that are significantly greater than the ORP characteristics of normal subjects known to be free of pyloric stenosis is indicative of the development or worsening of pyloric stenosis and dehydration and metabolic alkalosis in the subject. Similarly, an increase in the ORP characteristics of the subject over time is indicative of the development or worsening of pyloric stenosis in the subject. In order to determine the trend of the ORP characteristics in the subject over time, the ORP characteristics value of the subject may be checked, without limitation, every 1, 2, 3, 4, 5, or 6 minutes or days after the initial determination in order to compare and determine a trend in the ORP characteristics value of the patient.

The ORP characteristics of the subject may be obtained from a biological sample of the subject, including but not limited to blood, plasma, serum, saliva, tears, and mucus in a convenient and timely manner. The ORP characteristics of the subject may also be obtained from a tissue of the subject, including but not limited to, tissues of the digestive tract.

Medical Care Staging

The treatment capacity of certain specialty areas of a medical care facility may become overcrowded or may be under-utilized when patients are not appropriately and timely moved from one area to another depending on their medical condition and health status. For example, the emergency department in a hospital may become overcrowded when sick patients who have been evaluated by an emergency physician and admitted to a hospital, are left waiting for an inpatient hospital bed to become available. Alternatively, the full resources of the intensive care unit (ICU) in a hospital may be under-utilized if patients appropriately in need of such intensive care are not admitted and transferred from the emergency room to the intensive care unit. Further, discharge disposition decisions are important for appropriate utilization of medical facilities (e.g., hospitals), long term care facilities and skilled nursing facilities.

Another embodiment of this invention provides methods of diagnosing, evaluating or monitoring a patient within a medical care facility to determine the most appropriate transfer or discharge decision for the patient. In one embodiment, a patient is evaluated for ORP characteristics during diagnosis or treatment in one department or section of a medical care facility, such as a hospital or skilled nursing facility. A biological sample of the patient is tested for an ORP characteristic which is compared to a medical care staging reference value to determine the medical care staging status of the patient. Then a transfer decision for the patient is made based on the medical care staging status of the patient. The patient may be admitted to the medical facility, transferred from one department or unit of the facility to a different department or unit within the same facility, transferred from one department or unit of the facility to a different department or unit at a separate facility, not admitted to the medical facility or discharged from the medical care facility (e.g., discharged to home, a long term care facility, or a skilled nursing facility).

For example, ORP characteristic values of a patient in the emergency room department of a hospital that are significantly elevated compared to the ORP characteristic values of an individual or population of patients admitted to an intensive care unit of a medical care facility may be transferred from the emergency room to the intensive care unit. Alternatively, ORP characteristic values of a patient in the emergency room department of a hospital that are normal, or below the ORP characteristic values of an individual or population of patients admitted to an intensive care unit of a medical care facility, may be sent home from the emergency room and/or not transferred to the intensive care unit.

Similarly, ORP characteristic values of a patient in an intensive care unit of a medical care facility that are normal, or below the ORP characteristic values of an individual or population of patients in an intensive care unit of a medical care facility, may be transferred from the intensive care unit to another medical step down unit. Alternatively, ORP characteristic values of a patient in another department of a medical facility, such as a coronary care unit, that are significantly elevated compared to the ORP characteristic values of an individual or population of patients in that department or similar to the ORP characteristic values of an individual or population of patients admitted to an intensive care unit of a medical care facility, the patient may be transferred to the intensive care unit.

Such patient(s) may be evaluated for medical care staging ORP characteristic values at any time during their treatment at the facility in order to assess the need or ability to transfer to a different medical department.

Medical facilities may include, without limitation, hospitals, nursing homes, residential treatment centers, skilled nursing facilities, and geriatric care facilities.

Clinical Trials

Inclusion and exclusion criteria are the conditions that must be met in order to participate in a clinical trial, or the standards used to determine whether a person may be allowed to participate in a clinical trial. Important criteria used to determine a subject's appropriateness for clinical trial participation include the age, sex, stage of a disease (if any), treatment history, and other medical conditions of the potential study participant. In addition, the conduct of clinical trials involves the use of endpoints for example to determine therapeutic efficacy of a treatment being evaluated.

Another embodiment of this invention provides methods of evaluating or monitoring a subject enrolled in or under consideration for enrollment in a clinical trial. A biological sample of the subject is tested for an ORP characteristic which is compared to a clinical trial ORP reference value to determine the clinical trial status of the subject. The subject is then included in (or enrolled) or excluded (or withdrawn) from a clinical trial based on the trial status of the subject. Alternatively, the subject is assessed for therapeutic efficacy as part of the trial.

Subjects may be evaluated for clinical trial ORP characteristics at any time during their evaluation for, or enrollment in, a clinical trial in order to assess the inclusion or exclusion from the trial. Alternatively, subjects can be evaluated during a clinical trial as part of the trial.

For example, a subject being considered for inclusion in a clinical trial having ORP characteristic values that are significantly elevated compared to the ORP characteristic values of a normal individual or population of such subjects can be excluded or withdrawn from the clinical trial. Alternatively, ORP characteristic values of such a subject that are normal, or below the ORP characteristic values of an individual or population of patients included in such a clinical trial can be included or enrolled in the clinical trial.

As a further example, a subject in a clinical trial having ORP characteristic values as an endpoint in the trial can be evaluated in the trial as having met the endpoint. For example, the endpoint can be lowered or normal ORP values as an indicator of therapeutic efficacy of a treatment being tested. Alternatively, high ORP characteristic values can be endpoint of the time or amount of chemotherapy to be administered as a marker of induced toxicity.

Insurance Underwriting

When buying insurance, such as life insurance or disability insurance, a subject is typically required to undergo a medical exam for insurance underwriting purposes. When underwriting an insurance policy, insurers use mathematical and statistical methods to assess risk and measure the costs of alternative strategies with regard to the design, funding, accounting, administration, and maintenance or redesign of insurance plans, pension plans and annuities. Medical tests conducted by insurance companies on prospective policyholders often include analysis of blood and urine samples, and measurement of height, weight, blood pressure and pulse rate. The blood tests routinely screen for elevated blood sugar levels, abnormal liver and kidney functions, HIV, cocaine and cotinine. The results of these tests and measurements are compared to morbidity data to determine whether to insure the subject, and if so, how much to charge the subject.

Another embodiment of this invention provides methods of evaluating or monitoring a subject enrolled in, or under consideration for, enrollment in an insurance plan. A biological sample of the subject is tested for an ORP characteristic which is compared to an insurance ORP reference value to determine the insurable status of the subject. The subject is then included or enrolled in an insurance plan based on the insurable status of the subject and the rate or cost of the insurance is based on the insurable status of the subject. Alternatively, the subject is then excluded from an insurance plan based on the insurable status of the subject.

For example, a subject being considered for insurance having ORP characteristic values that are significantly elevated compared to the ORP characteristic values of an individual or population that is otherwise actuarially similar to the subject being considered can be denied insurance or be provided insurance at a higher rate or cost than individuals that are otherwise actuarially similar to the subject being considered. Alternatively, ORP characteristic values of such a subject being considered for insurance that are normal, or below the ORP characteristic values of an individual or population that is otherwise actuarially similar to the subject being considered can be provided insurance coverage. Alternatively, ORP characteristic values of such a subject being considered for insurance that are actuarially similar to the ORP characteristic values of an individual or population that is considered to have an elevated insurance risk can be denied coverage or provided insurance coverage at elevated cost.

Subjects may be evaluated for inclusion or exclusion using an insurance ORP reference value at any time during their evaluation for, or enrollment in, an insurance or pension plan in order to assess the inclusion or exclusion from the plan.

In each of these embodiments, the ORP value from the subject is preferably obtained by applying a current to a biological sample (a fluid or tissue sample) obtained from the subject and measuring a voltage across the sample over a period of time. The measured voltage is integrated over the period of time to obtain a value indicative of an oxidation reduction capacity (ORP).

Accordingly, the present invention has been described with some degree of particularity directed to the exemplary embodiments of the present invention. It should be appreciated though that modifications or changes may be made to the exemplary embodiments of the present invention without departing from the inventive concepts contained herein.

EXAMPLES

Example 1

This example evaluates methods of the present invention for use as a trauma frailty index by analysis of hip fracture patients. In particular, this example explores the use of oxidation reduction potential (ORP) and anti oxidant reserves (capacity) as biomarkers for a trauma frailty index. There are no measures available to rapidly assess trauma patient frailty. Widely-accepted measures, such as deficit accumulation calculations or self-reported surveys, are impractical within fast-paced trauma departments.

The Charlson Comorbidity Index (CCI) is a validated measure of comorbidities that provides insight to frailty. Oxidative stress occurs when the body produces too many damaging free radicals, causing or exacerbating disease. Oxidative stress measures were compared to the CCI to predict patient disposition and mortality.

Trauma patients were examined with traumatic hip fractures aged 65 and above, admitted between Jan. 1, 2010 and Jun. 30, 2012. Oxidative stress capacity levels were measured through use of a diagnostic oxidation reduction potential diagnostic system. ORP plasma samples were taken at admission (within 48 hours of admission) and discharge (within 48 hours of discharge). Differences between admission and discharge ORP were also calculated. Covariates included age-adjusted CCI values, comorbidity counts, and injury severity score (ISS). Outcome variables included patient disposition and mortality. Statistical analysis included Pearson correlations, generalized linear models and stepwise multivariate linear regression.

Patients with a non-fall or a non femoral injury or were transferred from an outside facility were excluded. 153 patients aged 65 and above with a traumatic hip fracture admitted to an ACS-verified, Level I trauma center were included in the analysis. Data were collected from a trauma registry.

Of 153 patients, 47% were above 85 years, 71% were female. The mean age-adjusted CCI was 5.4; median values for comorbidities and ISS were 2.0 and 9.0, respectively. 83% of patients were discharged to a skilled nursing facility (SNF), 10% went home, 5% went to hospice or rehabilitation, and 2% died. ORP capacity levels were not normally distributed, thus inverse capacity levels (ICL) was calculated (1/ORP capacity level). Admission ICL was correlated with comorbidity count ($p<0.05$), and discharge ICL was correlated with both age-adjusted CCI ($p<0.05$) and comorbidity counts ($p<0.05$). When measuring by percentiles, admission ICL was positively correlated with age ($p=0.05$) and comorbidity count ($p<0.05$); discharge ICL was correlated with comorbidity count ($p=0.05$). Patients with higher age-adjusted CCI or higher age were also more likely to have a sizeable increase in ICL ($p<0.05$ for both results). When examining outcomes, a lower ICL at admission reached a near-significant association with disposition to a SNF ($p=0.09$), and a larger change in ICL was also associated with discharge to SNF ($p<0.05$). The low number of deaths ($n=3$) prohibited analysis on mortality.

The association between discharge ORP and categorical covariates is shown below in Table 1:

TABLE 1

Association Between Discharge ORP and Categorical Covariates

| | Static ORP | Inverse Capacity ORP |
|---|---|---|
| Age 65-84 (n = 75) | 185.1 | 2.6 |
| Age ≥ 85 (n = 56) | 186.8 | 2.8 |
| p value | 0.63 | 0.46 |
| Male (n = 38) | 186 | 2.8 |
| Female (n = 93) | 185.8 | 2.7 |
| p value | 0.95 | 0.49 |
| Age-adjusted CCI < 6 (n = 75) | 184.2 | 2.6 |
| Age-adjusted CCI ≥ 6 (n = 55) | 187.4 | 2.9 |
| p value | 0.37 | 0.04 |
| ISS < 16 (n = 129) | 185.3 | 2.7 |
| ISS ≥ 16 (n = 2) | 218.4 | 3.5 |
| p value | 0.10 | <0.001 |
| Normal VS | 186.6 | 2.7 |
| Abnormal VS | 172.6 | 2.1 |
| p value | 0.34 | 0.22 |

A higher ISS and a higher CCI were associated with a higher inverse capacity ORP The association between ORP and discharge disposition is shown below in Table 2:

TABLE 2

Association Between ORP and Discharge Disposition

| | home/rehab (n = 20) | SNF (n = 147) | p value |
|---|---|---|---|
| Admission Static ORP | 168.4 (27.7) | 164.9 (23.2) | 0.60 |
| Admission Inverse Capacity ORP | 2.4 (1.0) | 2.0 (0.9) | 0.09 |
| Discharge Static ORP | 179.2 (17.9) | 186.2 (19.6) | 0.17 |
| Discharge Inverse Capacity ORP | 2.6 (0.8) | 2.7 (0.8) | 0.70 |
| Change in Static ORP | 10.7 (29.4) | 22.2 (21.8) | 0.18 |
| Change in Inverse Capacity ORP | 0.0 (1.0 | 0.7 (0.8) | 0.03 |

Mean (SD)

Skilled nursing facility (SNF) is a worse hospital disposition than home, nursing home, or a rehabilitation facility. A lower admission inverse capacity ORP was associated with disposition to SNF. A larger change in inverse capacity ORP was associated with discharge to SNF.

When clinicians consider the degree of frailty in older patients, treatment response, discharge options and end-of-life decisions may improve. This example demonstrates that the ICL increased with age-adjusted CCI and comorbidities, and changes in ICL values were associated with patient discharge. This example supports measuring oxidative stress capacity levels as a quick measure of frailty in trauma patients.

Example 2

This example demonstrates the use of ORP in adult patients with isolated Traumatic Brain Injury (TBI). The objective of this preliminary study was to examine the association between ORP, as measured by a device of the present invention, and various in-hospital patient outcomes in an isolated traumatic brain injury population.

A five-year prospective, observational cohort study was conducted at two Level I Trauma Centers in the United States, and included all admitted trauma patients who were at least 18 years old, suffered an isolated traumatic brain injury and provided their signed, informed consent. Plasma samples were collected in 2 mL sodium heparin tubes, and aliquoted into 0.2 mL volumes for ORP analysis. All samples were collected within 48 hours of injury or discharge. All ORP operators were blinded to the patients' clinical information. Each sample was tested using a system of the invention in duplicate. ORP duplicate tests reading more than 10 mV different were retested; samples of retests showing more than a 10 mV difference were excluded.

Static ORP (sORP) and inverse capacity ORP (cORP) were collected from the system, and the first, last, maximum and the change from first to last ORP values were analyzed. Student's T-tests, correlational analyses, and multivariate logistic regression were used to examine the association between ORP and various outcomes, including abbreviated injury severity (AIS) score of the head, in-hospital mortality, and discharge to a skilled nursing facility (SNF). All deaths were excluded from length of stay and complication analyses. Due to the investigative nature of this study, an alpha of 0.10 was used for all analyses.

There were 645 patients included in this study. A majority were <65 years (69%), male (61%), and the median head AIS was 3. There were a total of 11 deaths in the study, and 56 patients were discharged to a skilled nursing facility (SNF).

The results showed that after adjustment, a 20 mV increase in the first sORP were associated with a significant increase in the odds of in-hospital death (OR: 4.24, 95% CI: 1.2-15.3), being discharged to a SNF (OR: 1.28, 95% CI: 1.00-1.63), and significant decrease in the odds of having a complication (OR: 0.75, 95% CI: 0.63-0.89). After adjustment, a 20 mV increase in the last sORP and the maximum sORP were associated with significantly increased odds of being discharged to a SNF (OR: 2.28, 95% CI: 1.52-3.41; OR: 1.59, 95% CI: 1.20-2.09).

After adjustment, a 1-unit increase in the first inverse cORP were associated with significantly increased odds of being discharged to a SNF (OR: 1.97, 95% CI: 1.25-3.11), and a significantly decreased odds of having a complication (OR: 0.76, 95% CI: 0.61-0.94). After adjustment, a 1-unit increase in the last inverse cORP was associated with a significant increase in the odds of in-hospital mortality (OR: 5.05, 95% CI: 1.20-21.30), and a 1-unit increase in the maximum inverse cORP was associated with a significant increase in the odds of being discharged to a SNF (OR: 1.66, 95% CI: 1.21-2.28).

This investigative study demonstrates that deleterious changes in sORP and cORP are associated with poor patient outcomes. The ability of the redox system of the invention provides a useful point-of-care measure of ORP. Dichotomization points for sORP and inverse cORP will provide physicians with a useful guide for ascertaining the risk of certain patient outcomes.

Example 3

This example demonstrates the utility of monitoring sORP and cORP as a measure of frailty in an elderly population. Frailty can be consistently assessed through a Frailty Index, and increases in oxidative stress are associated with frailty. Therefore, ORP levels are associated with Frailty Index scores. This example will demonstrate the level of agreement between ORP-derived frailty and Frailty Index-derived frailty.

RedoxSYS™ is a small, portable reader that provides quantitative measurements of sORP and cORP. An ORP sensor is inserted into RedoxSYS™ and a plasma sample is added to the application spot. The test starts when the sample fills the reference electrode thereby completing the electrochemical circuit. After testing is complete, the reader displays the test results.

The percent agreement between ORP values and a Frailty Index is examined in two phases: the derivation phase and the validation phase. In the derivation phase, ranges of ORP values that best discriminate Frailty Index categories of non-frail or frail are derived from an initial population of 100 elderly subjects. The validation phase tests a second, separate population of 100 elderly subjects, and examines the percent agreement between the Frailty Index-assigned frailty and the ORP-assigned frailty. The FRAIL scale, the CSHA Clinical Frailty Scale, and the Charlson Comorbidity Index (CCI) are also examined. Each block of 100 patients is block-recruited in the following manner: 50 patients aged 65-84 and 50 patients aged 85 or older.

Once it has been determined that the subject meets the study enrollment criteria and written informed consent has been obtained, the following information is collected:

Demographics, medical history (including comorbidities, previous procedures, and vitamin usage).

Frailty Index (incorporated in patient survey, Table 4)

FRAIL Scale (incorporated in patient survey, Table 4)

CSHA Clinical Frailty Scale (Table 5)

A whole blood sample (~10 mL) is drawn into a sodium-heparinized anti-coagulated whole blood Vacutainer tube upon enrollment. The whole blood sample is analyzed at each site for sORP and cORP on RedoxSYS™ within two hours. The results of the RedoxSYS™ test are blinded to the medical team providing patient care and are not used for patient management.

In the first phase of the study, 100 elderly patients are examined. A receiver operator curve (ROC) is fit against ORP values and frailty to determine ORP dichotomization values for discriminating "frail" and "not frail." Frailty is assigned as follows: Frailty Index Score 0.0 to 0.35 is considered "not frail", while >0.35 is considered "frail".

In the second phase of the study, a second set of 100 elderly patients is categorized into "frail" and "not frail" categories based on their Frailty Index scores, as well as their ORP values (based on the ORP frailty cutoff value from the first phase of the study). Both the positive percent agreement and negative percent agreement is calculated for the ORP and Frailty Index-assigned categories.

The positive percent agreement is calculated as follows (see Table 3 below): TP/(TP+FN). The negative percent agreement is calculated as follows: TN/(TN+FP). A two-sided test, testing that the negative and positive percent agreements are not different from a proportion of 0.50 is done and the corresponding 95% confidence intervals and P-values are calculated.

TABLE 3

Frailty Index

|  |  | Not Frail | Frail |
| --- | --- | --- | --- |
| ORP | Not Frail | True Negative (TN) | False Negative (FN) |
|  | Frail | False Positive (FP) | True Positive (TP) |

Pearson correlation is used to examine the correlation between ORP and comorbidities, as follows:
CCI (defined continuously)
a-CCI (defined continuously)
Number of comorbidities present (defined continuously)
Pearson correlation is used to examine the correlation between ORP and the FRAIL scale and the CSHA Clinical Frailty Scale, as follows:
FRAIL scale (defined continuously)
CSHA Clinical Frailty Scale (defined continuously)
Poisson regression and linear regression is used to examine the association between ORP and comorbidities, as follows:
CCI (defined continuously)
a-CCI (defined continuously)
Number of comorbidities present (defined continuously)
Student's t-tests and logistic regression with crude and adjusted odds ratios (and 95% confidence intervals) is used to examine the association between ORP and comorbidities, as follows:
CCI≥5
CCI≥3
upper quartile of CCI (75$^{th}$ percentile)
presence of any comorbidity (0 vs. ≥1 comorbidity)
The percent positive agreement and percent negative agreement is used to examine the agreement between ORP and comorbidities, ORP and the FRAIL scale, and ORP and the CSHA Clinical Frailty Scale as follows:
The FRAIL scale (Frail=3-5, Not frail=0-2)
The CSHA Clinical Frailty Scale (Frail=5-7, Not frail=0-4)
CCI≥5
CCI≥3
upper quartile of CCI (75$^{th}$ percentile)
presence of any comorbidity (0 vs. ≥1 comorbidity)
Linear regression models are built for chronological age and Frailty Index Score. These models are used to output the calculated age ("biological age") for each participant based on their Frailty Index Score. Each participant's biological age is then subtracted from their chronological age. If the resulting value is negative, then the model indicates that that participant is expected to be older based on their Frailty Index Score; these patients are labeled as being frail. If after subtracting the biological age from the chronological age, the value is positive or zero, then the model indicates that that participant is expected to be younger or as old based on their Frailty Index Score; these patients are labeled as being non-frail. Using this new frailty categorization scheme, ORP cut-off values are determined that discriminate frail from non-frail using first phase data, and agreement levels are assessed using second phase data.

TABLE 4

Patient Survey

Difficulty with:

| 1. | Arthritis | Yes | No |
| --- | --- | --- | --- |
| 2. | Bladder/bowels | Yes | No |
| 3. | Cooking | Yes | No |
| 4. | Dementia | Yes | No |
| 5. | Dressing | Yes | No |
| 6. | Ear | Yes | No |
| 7. | Eating | Yes | No |
| 8. | Fatigue | Yes | No |
| 9. | Feet | Yes | No |
| 10. | Getting in or out bed | Yes | No |
| 11. | Going out | Yes | No |
| 12. | Hearing | Yes | No |
| 13. | Light housework | Yes | No |
| 14. | Managing money | Yes | No |
| 15. | Self-rated health | Yes | No |
| 16. | Shopping | Yes | No |
| 17. | Taking a bath | Yes | No |
| 18. | Taking medicine | Yes | No |
| 19. | Teeth | Yes | No |
| 20. | Using the telephone | Yes | No |
| 21. | Using the toilet | Yes | No |
| 22. | Vision | Yes | No |
| 23. | Walking around | Yes | No |

History of:

| 1. | Broken bones | Yes | No |
| --- | --- | --- | --- |
| 2. | Broken hip | Yes | No |
| 3. | Diabetes | Yes | No |
| 4. | Flu | Yes | No |
| 5. | Glaucoma | Yes | No |
| 6. | Heart attack | Yes | No |
| 7. | Hypertension | Yes | No |
| 8. | Parkinson's disease | Yes | No |
| 9. | Stomach problems | Yes | No |
| 10. | Stroke | Yes | No |
| 11. | Recent loss of weight | Yes | No |
| 12. | How much did the patient lose? (lbs) | | |
| 13. | Patient's current weight? (lbs) | | |

Can the patient:

| 14. | Climb one flight of stairs? | Yes | No |
| --- | --- | --- | --- |
| 15. | Walk one block? | Yes | No |
| 16. | What is the patient's current housing situation? | | |
| | a. | | Home |
| | b. | | Nursing Home |
| | c. | | Other: |

TABLE 5

CHSA Clinical Frailty Scale
The clinician will grade each patient based on their own understanding of the following scale.

1—Very fit. Robust, active, energetic, well-motivated and fit. These people exercise regularly and are in the most fit group for their age.
2—Well. Without active diseases but less fit that people in category 1.
3—Well, with treated comorbid disease. Disease symptoms are well-controlled compared to those in category 4.
4—Apparently vulnerable. Although not frankly dependent, these people commonly complain of being "slowed up" or have disease symptoms.
5—Mildly frail. With limited dependence on others for instrumental activities of daily living.
6—Moderately frail. Help is needed with both instrumental and non-instrumental activities of daily living.
7—Severely frail. Completely dependent on others for activities of daily living, or terminally ill.

The results of this Example show that measurement of sORP and cORP is useful in assessing frailty in an elderly population, and discriminating between frail and non-frail individuals. ORP measurements are also useful in identifying frailty comorbidities and determining differences between chronological age and biological age.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A system for identifying an oxidative capacity of a fluid, comprising:
   a fluid sample;
   a test strip, including:
      a reference cell;
      a sample chamber;
      a counter electrode, wherein a first portion of the counter electrode extends into the sample chamber;
      a working electrode, wherein a first portion of the working electrode extends into the sample chamber;
      a reference electrode, wherein the reference electrode is in electrical contact with the reference cell;
   a readout device, including:
      a first contact;
      a second contact;
      a third contact;
      a test signal power supply, wherein a first terminal of the test signal power supply is electrically connected to the first contact, and wherein a second terminal of the test signal power supply is electrically connected to the second contact;
      an electrometer, wherein a first input of the electrometer is electrically connected to the second contact, and wherein a second input of the electrometer is electrically connected to the third contact;
      memory;
      a processor, wherein with the first contact electrically connected to the counter electrode, the second contact electrically connected to the working electrode, and the third contact electrically connected to the reference electrode, and with the fluid sample in the sample chamber, the processor is configured to execute programming code stored in the memory to:
   operate the test signal power supply to supply a current across the sample chamber between the counter electrode and the working electrode for at least a first period of time;
   during the first period of time, monitor and/or record the voltage sensed by the electrometer;
   identify an inflection point in the voltage sensed by the electrometer; record the time at which the inflection point is identified: and
   integrate the current between a start time and the time at which the inflection point is reached to obtain an oxidation reduction capacity of the fluid sample.

2. The system of claim 1, wherein the processor is further configured to:
   operate the test signal power supply to supply the current at a static first level for a first time segment;
   after the first time segment, operate the test signal power supply to supply the current at a rising level for at least a second time segment.

3. The system of claim 1, wherein the readout device further includes:
   an output device, wherein the obtained oxidation reduction capacity of the fluid sample is output to a user by the output device.

4. The system of claim 3, wherein the obtained oxidation reduction capacity is output in units of $Coulombs^{-1}$.

* * * * *